(12) United States Patent
Knapp et al.

(10) Patent No.: US 8,480,559 B2
(45) Date of Patent: Jul. 9, 2013

(54) URETHRAL SUPPORT SYSTEM

(75) Inventors: Tracey E. Knapp, Lawrenceville, GA (US); Ken Butcher, Conyers, GA (US); Noah Meade, Atlanta, GA (US); Stephen Laffoon, Atlanta, GA (US); Charles Jacobs, Loganville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 395 days.

(21) Appl. No.: 12/441,123

(22) PCT Filed: Sep. 12, 2007

(86) PCT No.: PCT/US2007/078308
§ 371 (c)(1),
(2), (4) Date: May 24, 2010

(87) PCT Pub. No.: WO2008/033950
PCT Pub. Date: Mar. 20, 2008

(65) Prior Publication Data
US 2010/0234681 A1    Sep. 16, 2010

Related U.S. Application Data

(60) Provisional application No. 60/825,417, filed on Sep. 13, 2006, provisional application No. 60/922,745, filed on Apr. 9, 2007.

(51) Int. Cl.
*A61F 2/00* (2006.01)
*A61F 13/00* (2006.01)
*A61F 2/02* (2006.01)

(52) U.S. Cl.
USPC .............................................. 600/37; 600/30

(58) Field of Classification Search
USPC ....................................................... 600/37, 30
See application file for complete search history.

(56) References Cited

U.S. PATENT DOCUMENTS

| | | |
|---|---|---|
| 107,956 A | 10/1870 | Peoble |
| 1,393,107 A | 10/1921 | Fuller |
| 1,450,101 A | 3/1923 | Mathewson |
| 1,758,261 A | 5/1930 | Leland |
| 1,924,348 A | 8/1933 | Brown |

(Continued)

FOREIGN PATENT DOCUMENTS

| | | |
|---|---|---|
| CA | 2592617 C | 1/2012 |
| DE | 3223153 C1 | 8/1983 |

(Continued)

OTHER PUBLICATIONS

Cook Medical, Needle Suspension Product Pages, <<http://www.cookmedical.com>>, last accessed Aug. 13, 2008.

(Continued)

*Primary Examiner* — Christine Matthews
*Assistant Examiner* — Sunita Reddy
(74) *Attorney, Agent, or Firm* — Rutan & Tucker, LLP

(57) ABSTRACT

A urethral support system is described, including an introducer device and tissue implant. The introducer device may include a needle with multiple curves, some of the curves having multiple radii. A sheath assembly may be utilized to assist the passing of the tissue implant through a patient's tissue. The sheath assembly may include connectors configured to connect the sheath assembly to an end of the needle and a tab configured to detachably couple sheath sides over the tissue implant.

19 Claims, 14 Drawing Sheets

U.S. PATENT DOCUMENTS

| | | |
|---|---|---|
| 2,042,403 A | 5/1936 | Hrivnak |
| 2,097,018 A | 10/1937 | Chamberlin |
| 2,137,710 A | 11/1938 | Anderson |
| 2,240,330 A | 4/1941 | Flagg et al. |
| 2,427,176 A | 9/1947 | Aldeen |
| 2,518,994 A | 8/1950 | Miller |
| 2,641,249 A | 6/1953 | Brockman |
| 2,666,338 A | 1/1954 | Sandberg |
| 2,738,790 A | 3/1956 | Todt et al. |
| 3,124,136 A | 3/1964 | Usher |
| 3,126,600 A | 3/1964 | De Marre |
| 3,182,662 A | 5/1965 | Shirodkar |
| 3,249,104 A | 5/1966 | Johnstein |
| 3,311,110 A | 3/1967 | Singerman et al. |
| 3,340,494 A | 9/1967 | Gutshall |
| 3,384,073 A | 5/1968 | Van Winkle, Jr. |
| 3,453,729 A | 7/1969 | Larson |
| 3,472,232 A | 10/1969 | Earl |
| 3,580,313 A | 5/1971 | McKnight |
| 3,714,843 A | 2/1973 | Bracey |
| 3,739,430 A | 6/1973 | Kohke |
| 3,763,860 A | 10/1973 | Clarke |
| 3,777,737 A | 12/1973 | Bucalo |
| 3,789,828 A | 2/1974 | Schulte |
| 3,858,783 A | 1/1975 | Kapitanov et al. |
| 3,913,179 A | 10/1975 | Rhee |
| 3,924,633 A | 12/1975 | Cook et al. |
| 3,976,351 A | 8/1976 | Hopfe |
| 3,995,619 A | 12/1976 | Glatzer |
| 4,019,499 A | 4/1977 | Fitzgerald |
| 4,037,603 A | 7/1977 | Wendorff |
| 4,063,356 A | 12/1977 | Hepworth et al. |
| 4,069,956 A | 1/1978 | Shearer, Sr. et al. |
| 4,089,112 A | 5/1978 | Richards |
| 4,128,100 A | 12/1978 | Wendorff |
| 4,172,458 A | 10/1979 | Pereyra |
| 4,204,541 A | 5/1980 | Kapitanov |
| 4,232,445 A | 11/1980 | Ito |
| 4,233,734 A | 11/1980 | Bies |
| 4,235,238 A | 11/1980 | Ogiu et al. |
| 4,246,660 A | 1/1981 | Wevers |
| 4,255,881 A | 3/1981 | Fralish |
| 4,258,716 A | 3/1981 | Sutherland et al. |
| 4,265,231 A | 5/1981 | Scheller, Jr. et al. |
| 4,281,660 A | 8/1981 | Fujiwara |
| 4,322,885 A | 4/1982 | Osada et al. |
| 4,361,958 A | 12/1982 | Gilbert et al. |
| 4,409,866 A | 10/1983 | McBride |
| 4,441,497 A | 4/1984 | Paudler |
| 4,452,245 A | 6/1984 | Usher |
| 4,455,690 A | 6/1984 | Homsy |
| 4,467,802 A | 8/1984 | Maslanka et al. |
| 4,509,516 A | 4/1985 | Richmond |
| 4,524,771 A | 6/1985 | McGregor et al. |
| 4,632,100 A | 12/1986 | Somers et al. |
| 4,655,221 A | 4/1987 | Devereux |
| 4,679,453 A | 7/1987 | Morita et al. |
| 4,712,458 A | 12/1987 | Mally |
| 4,718,419 A | 1/1988 | Okada et al. |
| 4,741,335 A | 5/1988 | Okada et al. |
| 4,773,416 A | 9/1988 | Hourahane |
| 4,775,380 A | 10/1988 | Seedhom et al. |
| 4,784,139 A | 11/1988 | Demos |
| 4,799,484 A | 1/1989 | Smith et al. |
| 4,857,041 A | 8/1989 | Annis et al. |
| 4,865,031 A | 9/1989 | O'Keeffe |
| 4,911,164 A | 3/1990 | Roth |
| 4,920,986 A | 5/1990 | Biswas |
| 4,938,760 A | 7/1990 | Burton et al. |
| 4,946,467 A | 8/1990 | Ohi et al. |
| 5,013,292 A | 5/1991 | Lemay et al. |
| 5,013,316 A | 5/1991 | Goble et al. |
| 5,026,371 A | 6/1991 | Rydell et al. |
| 5,027,674 A | 7/1991 | Nolte et al. |
| 5,029,489 A | 7/1991 | Burmeister et al. |
| 5,053,043 A | 10/1991 | Gottesman et al. |
| 5,084,054 A | 1/1992 | Bencini et al. |
| 5,085,661 A | 2/1992 | Moss |
| 5,112,344 A | 5/1992 | Petros |
| 5,122,155 A | 6/1992 | Eberbach |
| 5,123,428 A | 6/1992 | Schwarz |
| 5,123,910 A | 6/1992 | McIntosh |
| 5,149,329 A | 9/1992 | Richardson |
| 5,152,749 A | 10/1992 | Giesy et al. |
| 5,152,778 A | 10/1992 | Bales, Jr. et al. |
| 5,163,942 A | 11/1992 | Rydell |
| 5,171,233 A | 12/1992 | Amplatz et al. |
| 5,171,314 A | 12/1992 | Dulebohn |
| 5,188,636 A | 2/1993 | Fedotov |
| 5,201,741 A | 4/1993 | Dulebohn |
| 5,207,694 A | 5/1993 | Broome |
| 5,209,756 A | 5/1993 | Seedhom et al. |
| 5,234,436 A | 8/1993 | Eaton et al. |
| 5,246,452 A | 9/1993 | Sinnott |
| 5,250,033 A | 10/1993 | Evans et al. |
| 5,256,133 A | 10/1993 | Spitz |
| 5,269,063 A | 12/1993 | Okada et al. |
| 5,281,237 A | 1/1994 | Gimpelson |
| 5,304,187 A | 4/1994 | Green et al. |
| 5,311,858 A | 5/1994 | Adair |
| 5,328,077 A | 7/1994 | Lou |
| 5,333,624 A | 8/1994 | Tovey |
| 5,334,185 A | 8/1994 | Giesy et al. |
| 5,336,239 A | 8/1994 | Gimpelson |
| 5,337,736 A | 8/1994 | Reddy |
| 5,342,371 A | 8/1994 | Welter et al. |
| 5,356,432 A | 10/1994 | Rutkow et al. |
| 5,362,294 A | 11/1994 | Seitzinger |
| 5,368,595 A | 11/1994 | Lewis |
| 5,368,602 A | 11/1994 | de la Torre |
| 5,380,334 A | 1/1995 | Torrie et al. |
| 5,383,904 A | 1/1995 | Totakura et al. |
| 5,386,836 A | 2/1995 | Biswas |
| 5,397,332 A | 3/1995 | Kammerer et al. |
| 5,397,353 A | 3/1995 | Oliver et al. |
| 5,403,328 A | 4/1995 | Shallman |
| 5,413,598 A | 5/1995 | Moreland |
| 5,439,467 A | 8/1995 | Benderev et al. |
| 5,447,512 A | 9/1995 | Wilson et al. |
| 5,456,721 A | 10/1995 | Legrand |
| 5,473,796 A | 12/1995 | Fusillo |
| 5,474,543 A | 12/1995 | McKay |
| 5,486,183 A | 1/1996 | Middleman et al. |
| 5,497,553 A | 3/1996 | Chong et al. |
| 5,499,991 A | 3/1996 | Garman et al. |
| 5,500,000 A | 3/1996 | Feagin et al. |
| 5,501,692 A | 3/1996 | Riza |
| 5,502,896 A | 4/1996 | Chen et al. |
| 5,509,900 A | 4/1996 | Kirkman |
| 5,520,700 A | 5/1996 | Beyar et al. |
| 5,520,703 A | 5/1996 | Essig et al. |
| 5,522,833 A | 6/1996 | Stephens et al. |
| 5,542,948 A | 8/1996 | Weaver et al. |
| 5,544,664 A | 8/1996 | Benderev et al. |
| 5,549,619 A | 8/1996 | Peters et al. |
| 5,549,676 A | 8/1996 | Johnson |
| 5,562,678 A | 10/1996 | Booker |
| 5,562,685 A | 10/1996 | Mollenauer et al. |
| 5,562,688 A | 10/1996 | Riza |
| 5,562,689 A | 10/1996 | Green et al. |
| 5,569,269 A | 10/1996 | Hart et al. |
| 5,571,139 A | 11/1996 | Jenkins, Jr. |
| 5,573,530 A | 11/1996 | Fleury et al. |
| 5,591,163 A | 1/1997 | Thompson |
| 5,601,558 A | 2/1997 | Torrie et al. |
| 5,611,515 A | 3/1997 | Benderev et al. |
| 5,628,756 A | 5/1997 | Barker, Jr. et al. |
| 5,633,286 A | 5/1997 | Chen |
| 5,640,886 A | 6/1997 | Lai et al. |
| 5,643,320 A | 7/1997 | Lower et al. |
| 5,647,836 A | 7/1997 | Blake, III et al. |
| 5,655,270 A | 8/1997 | Boisvert |
| 5,662,683 A | 9/1997 | Kay |
| 5,667,513 A | 9/1997 | Torrie et al. |
| 5,669,935 A | 9/1997 | Rosenman et al. |
| 5,683,349 A | 11/1997 | Makower et al. |
| 5,689,860 A | 11/1997 | Matoba et al. |

| Patent No. | Date | Inventor |
|---|---|---|
| 5,693,072 A | 12/1997 | McIntosh |
| 5,702,397 A | 12/1997 | Goble et al. |
| 5,755,728 A | 5/1998 | Maki |
| 5,774,994 A | 7/1998 | Stein et al. |
| 5,792,142 A | 8/1998 | Galitzer |
| 5,807,403 A | 9/1998 | Beyar et al. |
| 5,810,882 A | 9/1998 | Bolduc et al. |
| 5,817,104 A | 10/1998 | Bilitz et al. |
| 5,817,128 A | 10/1998 | Storz et al. |
| 5,830,220 A | 11/1998 | Wan et al. |
| 5,836,053 A | 11/1998 | Davignon et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,846,248 A | 12/1998 | Chu et al. |
| 5,860,425 A | 1/1999 | Benderev et al. |
| 5,862,596 A | 1/1999 | Chung et al. |
| 5,864,952 A | 2/1999 | Chung et al. |
| 5,899,909 A | 5/1999 | Claren et al. |
| 5,904,692 A | 5/1999 | Steckel et al. |
| 5,904,696 A | 5/1999 | Rosenman |
| 5,910,148 A | 6/1999 | Reimels et al. |
| 5,919,232 A | 7/1999 | Chaffringeon et al. |
| 5,934,283 A | 8/1999 | Willem et al. |
| 5,935,122 A | 8/1999 | Fourkas et al. |
| 5,935,138 A | 8/1999 | McJames, II et al. |
| 5,944,732 A | 8/1999 | Raulerson et al. |
| 5,947,978 A | 9/1999 | Holsinger |
| 5,961,526 A | 10/1999 | Chu et al. |
| 5,968,008 A | 10/1999 | Grams |
| 5,971,967 A | 10/1999 | Willard |
| 5,972,000 A | 10/1999 | Beyar et al. |
| 5,987,751 A | 11/1999 | Chung et al. |
| 5,988,171 A | 11/1999 | Sohn et al. |
| 5,992,269 A | 11/1999 | Puig et al. |
| 5,993,459 A | 11/1999 | Larsen et al. |
| 5,997,554 A | 12/1999 | Thompson |
| 6,005,191 A | 12/1999 | Tzeng et al. |
| 6,006,433 A | 12/1999 | Baltazar |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,048,351 A | 4/2000 | Gordon et al. |
| 6,048,354 A | 4/2000 | Lawrence |
| 6,050,937 A | 4/2000 | Benderev |
| 6,053,925 A | 4/2000 | Barnhart |
| 6,053,935 A | 4/2000 | Brenneman et al. |
| 6,056,688 A | 5/2000 | Benderev et al. |
| 6,059,796 A | 5/2000 | Bilitz et al. |
| 6,063,094 A | 5/2000 | Rosenberg et al. |
| 6,068,591 A | 5/2000 | Bruckner et al. |
| 6,068,648 A | 5/2000 | Cole et al. |
| 6,071,290 A | 6/2000 | Compton |
| 6,074,341 A | 6/2000 | Anderson et al. |
| 6,086,591 A | 7/2000 | Bojarski |
| 6,092,955 A | 7/2000 | Chartrain et al. |
| 6,096,041 A | 8/2000 | Gellman et al. |
| 6,096,060 A | 8/2000 | Fitts et al. |
| 6,099,538 A | 8/2000 | Moses et al. |
| 6,106,545 A | 8/2000 | Egan |
| 6,110,101 A | 8/2000 | Tihon et al. |
| 6,117,067 A | 9/2000 | Gil-Vernet |
| 6,117,162 A | 9/2000 | Schmieding et al. |
| 6,168,611 B1 | 1/2001 | Rizvi |
| 6,171,315 B1 | 1/2001 | Chu et al. |
| 6,197,036 B1 | 3/2001 | Tripp et al. |
| 6,200,330 B1 | 3/2001 | Benderev et al. |
| 6,210,416 B1 | 4/2001 | Chu et al. |
| 6,221,005 B1 | 4/2001 | Bruckner et al. |
| 6,221,060 B1 | 4/2001 | Willard |
| 6,226,873 B1 | 5/2001 | Okumura et al. |
| 6,235,026 B1 | 5/2001 | Smith |
| 6,273,852 B1 | 8/2001 | Lehe et al. |
| 6,290,702 B1 | 9/2001 | Fucci et al. |
| 6,293,961 B2 | 9/2001 | Schwartz et al. |
| 6,302,840 B1 | 10/2001 | Benderev |
| 6,306,079 B1 | 10/2001 | Trabucco |
| 6,306,159 B1 | 10/2001 | Schwartz et al. |
| 6,312,448 B1 | 11/2001 | Bonutti |
| 6,315,782 B1 | 11/2001 | Chu et al. |
| 6,319,271 B1 | 11/2001 | Schwartz et al. |
| 6,322,492 B1 | 11/2001 | Kovac |
| 6,328,686 B1 | 12/2001 | Kovac |
| 6,328,744 B1 | 12/2001 | Harari et al. |
| 6,328,758 B1 | 12/2001 | Tornier et al. |
| 6,334,446 B1 | 1/2002 | Beyar |
| 6,336,731 B1 | 1/2002 | Chien |
| 6,346,109 B1 | 2/2002 | Fucci et al. |
| 6,346,115 B1 | 2/2002 | Lawrence |
| 6,352,553 B1 | 3/2002 | van der Burg et al. |
| 6,355,065 B1 | 3/2002 | Gabbay |
| 6,358,197 B1 | 3/2002 | Silverman et al. |
| 6,367,353 B2 | 4/2002 | Brucart Puig et al. |
| 6,371,963 B1 | 4/2002 | Nishtala et al. |
| 6,375,661 B2 | 4/2002 | Chu et al. |
| 6,382,214 B1 | 5/2002 | Raz et al. |
| D458,679 S | 6/2002 | Thompson et al. |
| 6,406,423 B1 | 6/2002 | Scetbon |
| 6,406,480 B1 | 6/2002 | Beyar et al. |
| 6,409,733 B1 | 6/2002 | Conlon et al. |
| 6,423,080 B1 | 7/2002 | Gellman et al. |
| 6,432,123 B2 | 8/2002 | Schwartz et al. |
| 6,440,154 B2 | 8/2002 | Gellman et al. |
| 6,475,139 B1 | 11/2002 | Miller |
| 6,478,727 B2 | 11/2002 | Scetbon et al. |
| 6,478,803 B1 | 11/2002 | Kapec et al. |
| 6,482,214 B1 | 11/2002 | Sidor, Jr. et al. |
| 6,491,703 B1 | 12/2002 | Ulmsten et al. |
| 6,491,714 B1 | 12/2002 | Bennett |
| 6,494,887 B1 | 12/2002 | Kaladelfos et al. |
| 6,494,906 B1 | 12/2002 | Owens |
| 6,502,578 B2 | 1/2003 | Raz et al. |
| 6,506,190 B1 | 1/2003 | Walshe |
| 6,511,499 B2 | 1/2003 | Schmieding et al. |
| 6,517,552 B1 | 2/2003 | Nord et al. |
| 6,530,943 B1 | 3/2003 | Hoepffner et al. |
| 6,537,198 B1 | 3/2003 | Vidlund et al. |
| 6,544,267 B1 | 4/2003 | Cole et al. |
| 6,553,674 B1 | 4/2003 | Budrow |
| 6,554,842 B2 | 4/2003 | Heuser et al. |
| 6,569,188 B2 | 5/2003 | Grafton et al. |
| 6,575,976 B2 | 6/2003 | Grafton |
| 6,575,984 B2 | 6/2003 | Beyar et al. |
| 6,575,998 B2 | 6/2003 | Beyar et al. |
| 6,582,443 B2 | 6/2003 | Cabak et al. |
| 6,591,838 B2 | 7/2003 | Durgin |
| 6,592,515 B2 | 7/2003 | Thierfelder et al. |
| 6,592,610 B2 | 7/2003 | Beyar |
| 6,596,001 B2 | 7/2003 | Stormby et al. |
| 6,605,097 B1 | 8/2003 | Lehe et al. |
| 6,612,977 B2 | 9/2003 | Staskin et al. |
| 6,626,917 B1 | 9/2003 | Craig |
| 6,638,209 B2 | 10/2003 | Landgrebe et al. |
| 6,638,210 B2 | 10/2003 | Berger |
| 6,638,211 B2 | 10/2003 | Suslian et al. |
| 6,638,286 B1 | 10/2003 | Burbank et al. |
| 6,641,524 B2 | 11/2003 | Kovac |
| 6,641,525 B2 | 11/2003 | Rocheleau et al. |
| 6,652,450 B2 | 11/2003 | Neisz et al. |
| 6,652,537 B2 | 11/2003 | Mercereau et al. |
| 6,656,183 B2 | 12/2003 | Colleran et al. |
| 6,663,633 B1 | 12/2003 | Pierson, III |
| 6,663,645 B2 | 12/2003 | Nishtala et al. |
| 6,673,010 B2 | 1/2004 | Skiba et al. |
| 6,675,483 B2 | 1/2004 | Bond et al. |
| 6,676,668 B2 | 1/2004 | Mercereau et al. |
| 6,685,629 B2 | 2/2004 | Therin |
| 6,689,047 B2 | 2/2004 | Gellman |
| 6,691,711 B2 | 2/2004 | Raz et al. |
| 6,702,827 B1 | 3/2004 | Lund et al. |
| 6,708,410 B2 | 3/2004 | Okada et al. |
| 6,712,830 B2 | 3/2004 | Esplin |
| 6,730,097 B2 | 5/2004 | Dennis |
| 6,730,110 B1 | 5/2004 | Harari et al. |

| Patent | Date | Name |
|---|---|---|
| 6,736,854 B2 | 5/2004 | Vadurro et al. |
| 6,737,371 B1 | 5/2004 | Planck et al. |
| 6,746,472 B2 | 6/2004 | Frazier et al. |
| 6,752,814 B2 | 6/2004 | Gellman et al. |
| 6,755,781 B2 | 6/2004 | Gellman |
| 6,761,722 B2 | 7/2004 | Cole et al. |
| 6,789,326 B1 | 9/2004 | Huang et al. |
| 6,802,807 B2 | 10/2004 | Anderson et al. |
| 6,808,486 B1 | 10/2004 | O'Donnell |
| 6,808,487 B2 | 10/2004 | Migliari et al. |
| 6,835,193 B2 | 12/2004 | Epstein et al. |
| 6,843,792 B2 | 1/2005 | Nishtala et al. |
| 6,872,227 B2 | 3/2005 | Sump et al. |
| 6,878,134 B2 | 4/2005 | Rogers et al. |
| 6,881,184 B2 | 4/2005 | Zappala |
| 6,908,425 B2 | 6/2005 | Luscombe |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,960,160 B2 | 11/2005 | Browning et al. |
| 6,966,113 B2 | 11/2005 | Fossella |
| 6,971,390 B1 | 12/2005 | Vasek et al. |
| 6,971,986 B2 | 12/2005 | Staskin et al. |
| 6,986,781 B2 | 1/2006 | Smith |
| 6,987,995 B2 | 1/2006 | Drysen |
| 6,991,597 B2 | 1/2006 | Gellman et al. |
| 7,014,607 B2 | 3/2006 | Gellman |
| 7,025,063 B2 | 4/2006 | Snitkin et al. |
| 7,025,756 B2 | 4/2006 | Frazier et al. |
| 7,025,772 B2 | 4/2006 | Gellman et al. |
| 7,033,380 B2 | 4/2006 | Schwartz et al. |
| 7,037,255 B2 | 5/2006 | Inman et al. |
| 7,037,307 B2 | 5/2006 | Dennis |
| 7,037,324 B2 | 5/2006 | Martinek |
| 7,044,905 B2 | 5/2006 | Vidlund et al. |
| 7,048,682 B2 | 5/2006 | Neisz et al. |
| 7,052,495 B2 | 5/2006 | Smith |
| 7,056,333 B2 | 6/2006 | Walshe |
| 7,063,716 B2 | 6/2006 | Cunningham |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,648 B2 | 8/2006 | Yu et al. |
| 7,087,065 B2 | 8/2006 | Ulmsten et al. |
| 7,094,199 B2 | 8/2006 | Petros et al. |
| 7,101,378 B2 | 9/2006 | Salameh et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin et al. |
| 7,163,506 B2 | 1/2007 | Grise |
| 7,198,597 B2 | 4/2007 | Siegel et al. |
| 7,204,801 B2 | 4/2007 | Grocela |
| 7,204,802 B2 | 4/2007 | De Leval et al. |
| RE39,626 E | 5/2007 | Tihon |
| D543,626 S | 5/2007 | Watschke et al. |
| 7,217,264 B2 | 5/2007 | Gobron et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,259 B2 | 7/2007 | Smith et al. |
| 7,261,723 B2 | 8/2007 | Smith et al. |
| 7,267,645 B2 | 9/2007 | Anderson et al. |
| 7,285,086 B2 | 10/2007 | Smith et al. |
| 7,288,063 B2 | 10/2007 | Petros et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,338,432 B2 | 3/2008 | Valtchev |
| 7,347,812 B2 | 3/2008 | Mellier et al. |
| 7,347,813 B2 | 3/2008 | Claren et al. |
| 7,351,196 B2 | 4/2008 | Goldmann et al. |
| 7,351,197 B2 | 4/2008 | Montpetit et al. |
| 7,357,773 B2 | 4/2008 | Watschke |
| 7,364,541 B2 | 4/2008 | Chu et al. |
| 7,371,245 B2 | 5/2008 | Evans et al. |
| 7,387,634 B2 | 6/2008 | Benderev |
| 7,402,133 B2 | 7/2008 | Chu et al. |
| 7,404,819 B1 | 7/2008 | Darios et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal et al. |
| 7,500,945 B2 | 3/2009 | Cox et al. |
| 7,527,588 B2 | 5/2009 | Zaddem et al. |
| 7,588,598 B2 | 9/2009 | Delorme et al. |
| 7,611,454 B2 | 11/2009 | De Leval |
| 7,621,864 B2 | 11/2009 | Suslian et al. |
| 7,621,865 B2 | 11/2009 | Gellman et al. |
| 7,628,156 B2 | 12/2009 | Astani et al. |
| 7,658,743 B2 | 2/2010 | Ulmsten |
| 7,691,050 B2 | 4/2010 | Gellman et al. |
| 7,691,052 B2 | 4/2010 | Gellman et al. |
| 7,691,110 B2 | 4/2010 | Secrest et al. |
| 7,722,527 B2 | 5/2010 | Bouchier et al. |
| 7,771,345 B1 | 8/2010 | O'Donnell |
| 7,789,821 B2 | 9/2010 | Browning |
| 7,867,161 B2 | 1/2011 | Staskin et al. |
| 7,878,969 B2 | 2/2011 | Chu et al. |
| 7,896,848 B2 | 3/2011 | Charukhchian |
| 7,981,023 B2 | 7/2011 | Nowlin et al. |
| 7,988,615 B2 | 8/2011 | Anderson et al. |
| 8,007,430 B2 | 8/2011 | Browning |
| 8,033,983 B2 | 10/2011 | Chu et al. |
| 8,057,383 B2 | 11/2011 | Weiser et al. |
| 8,092,366 B2 | 1/2012 | Evans |
| 8,097,007 B2 | 1/2012 | Evans et al. |
| 8,123,671 B2 | 2/2012 | Evans |
| 8,206,280 B2 | 6/2012 | Evans et al. |
| 2001/0000533 A1 | 4/2001 | Kovac |
| 2001/0008549 A1 | 7/2001 | Hashimoto |
| 2001/0010008 A1 | 7/2001 | Gellman et al. |
| 2001/0049467 A1 | 12/2001 | Lehe et al. |
| 2001/0051807 A1 | 12/2001 | Grafton |
| 2001/0053916 A1 | 12/2001 | Rioux |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0052653 A1 | 5/2002 | Durgin |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0091373 A1 | 7/2002 | Berger |
| 2002/0091391 A1 | 7/2002 | Cole et al. |
| 2002/0095181 A1 | 7/2002 | Beyar |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0156489 A1 | 10/2002 | Gellman et al. |
| 2002/0165566 A1 | 11/2002 | Ulmsten |
| 2002/0188169 A1 | 12/2002 | Kammerer et al. |
| 2002/0188301 A1 | 12/2002 | Dallara et al. |
| 2003/0004395 A1 | 1/2003 | Therin |
| 2003/0009181 A1* | 1/2003 | Gellman et al. ............ 606/151 |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0036770 A1 | 2/2003 | Markman |

| | | | |
|---|---|---|---|
| 2003/0045774 A1 | 3/2003 | Staskin et al. | |
| 2003/0045892 A1 | 3/2003 | Kaladelfos | |
| 2003/0050530 A1 | 3/2003 | Neisz et al. | |
| 2003/0065246 A1* | 4/2003 | Inman et al. .................. 600/29 | |
| 2003/0065402 A1 | 4/2003 | Anderson et al. | |
| 2003/0078604 A1 | 4/2003 | Walshe | |
| 2003/0088250 A1 | 5/2003 | Colleran et al. | |
| 2003/0130670 A1 | 7/2003 | Anderson et al. | |
| 2003/0135239 A1 | 7/2003 | Gabriel et al. | |
| 2003/0149440 A1 | 8/2003 | Kammerer et al. | |
| 2003/0171644 A1 | 9/2003 | Anderson et al. | |
| 2003/0176762 A1 | 9/2003 | Kammerer | |
| 2003/0176875 A1 | 9/2003 | Anderson et al. | |
| 2003/0191360 A1 | 10/2003 | Browning | |
| 2003/0199732 A1 | 10/2003 | Suslian et al. | |
| 2003/0212305 A1 | 11/2003 | Anderson et al. | |
| 2003/0216693 A1 | 11/2003 | Mickley | |
| 2003/0220538 A1 | 11/2003 | Jacquetin | |
| 2003/0225424 A1 | 12/2003 | Benderev | |
| 2003/0229350 A1 | 12/2003 | Kay | |
| 2004/0006353 A1 | 1/2004 | Bosley et al. | |
| 2004/0015048 A1 | 1/2004 | Neisz et al. | |
| 2004/0015057 A1 | 1/2004 | Rocheleau et al. | |
| 2004/0039246 A1 | 2/2004 | Gellman et al. | |
| 2004/0039453 A1 | 2/2004 | Anderson et al. | |
| 2004/0040159 A1 | 3/2004 | Fossella | |
| 2004/0044364 A1 | 3/2004 | DeVries et al. | |
| 2004/0059336 A1 | 3/2004 | Lombardo et al. | |
| 2004/0068159 A1 | 4/2004 | Neisz et al. | |
| 2004/0073219 A1 | 4/2004 | Skiba et al. | |
| 2004/0073234 A1 | 4/2004 | Chu et al. | |
| 2004/0087970 A1 | 5/2004 | Chu et al. | |
| 2004/0087980 A1 | 5/2004 | Ford et al. | |
| 2004/0097974 A1 | 5/2004 | De Leval | |
| 2004/0097975 A1 | 5/2004 | Rose | |
| 2004/0106845 A1 | 6/2004 | Anderson et al. | |
| 2004/0106847 A1 | 6/2004 | Benderev | |
| 2004/0106925 A1 | 6/2004 | Culbert | |
| 2004/0111895 A1 | 6/2004 | Huang | |
| 2004/0116774 A1 | 6/2004 | Migliari | |
| 2004/0116944 A1 | 6/2004 | Chu et al. | |
| 2004/0122474 A1 | 6/2004 | Gellman et al. | |
| 2004/0406847 | 6/2004 | Benderev | |
| 2004/0133217 A1* | 7/2004 | Watschke ................. 606/148 | |
| 2004/0144395 A1* | 7/2004 | Evans et al. .................. 128/885 | |
| 2004/0153008 A1 | 8/2004 | Sharf et al. | |
| 2004/0153074 A1 | 8/2004 | Bojarski et al. | |
| 2004/0153103 A1 | 8/2004 | Schwartz et al. | |
| 2004/0172048 A1 | 9/2004 | Browning | |
| 2004/0209538 A1 | 10/2004 | Klinge et al. | |
| 2004/0220595 A1 | 11/2004 | Frazier et al. | |
| 2004/0225181 A1 | 11/2004 | Chu et al. | |
| 2004/0225301 A1 | 11/2004 | Roop et al. | |
| 2004/0230206 A1 | 11/2004 | Gellman et al. | |
| 2004/0230207 A1 | 11/2004 | Gellman et al. | |
| 2004/0231678 A1 | 11/2004 | Fierro | |
| 2004/0249240 A1 | 12/2004 | Goldmann et al. | |
| 2004/0249396 A1 | 12/2004 | Lund et al. | |
| 2004/0249473 A1 | 12/2004 | Delorme et al. | |
| 2004/0254609 A1 | 12/2004 | Esplin | |
| 2004/0267088 A1 | 12/2004 | Kammerer | |
| 2005/0004576 A1 | 1/2005 | Benderev | |
| 2005/0021086 A1 | 1/2005 | De Leval | |
| 2005/0028380 A1 | 2/2005 | Fossella | |
| 2005/0033365 A1 | 2/2005 | Courage | |
| 2005/0038370 A1 | 2/2005 | Kuth et al. | |
| 2005/0043580 A1 | 2/2005 | Watschke et al. | |
| 2005/0065395 A1* | 3/2005 | Mellier .................. 600/37 | |
| 2005/0070829 A1 | 3/2005 | Therin et al. | |
| 2005/0075654 A1 | 4/2005 | Kelleher | |
| 2005/0075660 A1 | 4/2005 | Chu et al. | |
| 2005/0085831 A1 | 4/2005 | Rioux | |
| 2005/0090706 A1 | 4/2005 | Gellman et al. | |
| 2005/0090841 A1 | 4/2005 | Morrison | |
| 2005/0101834 A1 | 5/2005 | Merade | |
| 2005/0101973 A1 | 5/2005 | Smith et al. | |
| 2005/0107660 A1 | 5/2005 | Valtchev | |
| 2005/0113845 A1 | 5/2005 | Griego et al. | |
| 2005/0131274 A1 | 6/2005 | Suslian et al. | |
| 2005/0131391 A1 | 6/2005 | Chu | |
| 2005/0131392 A1 | 6/2005 | Chu et al. | |
| 2005/0131393 A1 | 6/2005 | Chu et al. | |
| 2005/0131429 A1 | 6/2005 | Ho et al. | |
| 2005/0143618 A1 | 6/2005 | Anderson et al. | |
| 2005/0148813 A1 | 7/2005 | Claren et al. | |
| 2005/0149122 A1 | 7/2005 | McDevitt et al. | |
| 2005/0177022 A1 | 8/2005 | Chu et al. | |
| 2005/0228413 A1 | 10/2005 | Binmoeller et al. | |
| 2005/0234291 A1 | 10/2005 | Gingras | |
| 2005/0240076 A1 | 10/2005 | Neisz et al. | |
| 2005/0251083 A1 | 11/2005 | Carr-Brendel et al. | |
| 2005/0251159 A1 | 11/2005 | Ewers et al. | |
| 2005/0251177 A1 | 11/2005 | Saadat et al. | |
| 2005/0251202 A1 | 11/2005 | Ewers et al. | |
| 2005/0251210 A1 | 11/2005 | Westra et al. | |
| 2005/0256366 A1 | 11/2005 | Chu | |
| 2005/0256530 A1 | 11/2005 | Petros | |
| 2005/0261545 A1 | 11/2005 | Gellman et al. | |
| 2005/0273138 A1 | 12/2005 | To et al. | |
| 2005/0277806 A1 | 12/2005 | Cristalli | |
| 2005/0277807 A1 | 12/2005 | MacLean et al. | |
| 2005/0277966 A1 | 12/2005 | Ewers et al. | |
| 2005/0277981 A1 | 12/2005 | Maahs et al. | |
| 2005/0283040 A1 | 12/2005 | Greenhalgh | |
| 2005/0288689 A1 | 12/2005 | Kammerer et al. | |
| 2006/0015001 A1 | 1/2006 | Staskin et al. | |
| 2006/0015069 A1* | 1/2006 | Evans et al. .................. 604/164.04 | |
| 2006/0025649 A1 | 2/2006 | Smith et al. | |
| 2006/0041185 A1 | 2/2006 | Browning | |
| 2006/0058574 A1 | 3/2006 | Priewe et al. | |
| 2006/0058575 A1 | 3/2006 | Zaddem et al. | |
| 2006/0058578 A1 | 3/2006 | Browning | |
| 2006/0059693 A1 | 3/2006 | Fossella | |
| 2006/0059695 A1 | 3/2006 | Levine et al. | |
| 2006/0063968 A1 | 3/2006 | Anderson et al. | |
| 2006/0089524 A1 | 4/2006 | Chu | |
| 2006/0089525 A1 | 4/2006 | Mamo et al. | |
| 2006/0100628 A1 | 5/2006 | Martinek | |
| 2006/0106277 A1 | 5/2006 | Romero Maroto | |
| 2006/0116719 A1 | 6/2006 | Martinek | |
| 2006/0122457 A1 | 6/2006 | Kovac et al. | |
| 2006/0130848 A1 | 6/2006 | Carey | |
| 2006/0134159 A1 | 6/2006 | Nicita | |
| 2006/0149123 A1 | 7/2006 | Vidlund et al. | |
| 2006/0173237 A1 | 8/2006 | Jacquetin | |
| 2006/0173468 A1 | 8/2006 | Simmon et al. | |
| 2006/0173471 A1 | 8/2006 | Carr, Jr. et al. | |
| 2006/0173864 A1 | 8/2006 | Dart et al. | |
| 2006/0183966 A1 | 8/2006 | Neisz et al. | |
| 2006/0184234 A1 | 8/2006 | Frazier et al. | |
| 2006/0195007 A1* | 8/2006 | Anderson et al. .................. 600/29 | |
| 2006/0195010 A1 | 8/2006 | Arnal et al. | |
| 2006/0195011 A1 | 8/2006 | Arnal et al. | |
| 2006/0195013 A1 | 8/2006 | Gellman et al. | |
| 2006/0196137 A1 | 9/2006 | Brenzel et al. | |
| 2006/0199994 A1 | 9/2006 | Inman et al. | |
| 2006/0199996 A1 | 9/2006 | Caraballo et al. | |
| 2006/0201519 A1 | 9/2006 | Frazier et al. | |
| 2006/0205995 A1 | 9/2006 | Browning | |
| 2006/0205998 A1 | 9/2006 | Li et al. | |
| 2006/0207606 A1 | 9/2006 | Roue et al. | |
| 2006/0217762 A1 | 9/2006 | Maahs et al. | |
| 2006/0229493 A1 | 10/2006 | Weiser et al. | |
| 2006/0229596 A1 | 10/2006 | Weiser et al. | |
| 2006/0235262 A1* | 10/2006 | Arnal et al. .................. 600/30 | |
| 2006/0235447 A1 | 10/2006 | Walshe | |
| 2006/0247490 A1 | 11/2006 | Merade et al. | |
| 2006/0252980 A1 | 11/2006 | Arnal et al. | |
| 2006/0258897 A1 | 11/2006 | Petros et al. | |
| 2006/0258898 A1 | 11/2006 | Montpetit et al. | |
| 2006/0260618 A1 | 11/2006 | Hodroff et al. | |
| 2006/0264698 A1 | 11/2006 | Kondonis et al. | |
| 2006/0287571 A1 | 12/2006 | Gozzi et al. | |
| 2007/0010830 A1 | 1/2007 | Gellman et al. | |
| 2007/0015957 A1 | 1/2007 | Li | |
| 2007/0021649 A1 | 1/2007 | Nowlin et al. | |
| 2007/0021650 A1 | 1/2007 | Rocheleau et al. | |
| 2007/0021686 A1 | 1/2007 | Gellman et al. | |

| | | | | | | |
|---|---|---|---|---|---|---|
| 2007/0032695 | A1 | 2/2007 | Weiser | EP | 0913162 A1 | 5/1999 |
| 2007/0038017 | A1 | 2/2007 | Chu | EP | 0941712 A1 | 9/1999 |
| 2007/0038018 | A1 | 2/2007 | Chu | EP | 0983033 B1 | 3/2000 |
| 2007/0043255 | A1 | 2/2007 | O'Donnell | EP | 1018980 B1 | 7/2000 |
| 2007/0043336 | A1 | 2/2007 | Griffin et al. | EP | 1093758 | 4/2001 |
| 2007/0049790 | A1 | 3/2007 | Wagner et al. | EP | 1151722 | 11/2001 |
| 2007/0049791 | A1 | 3/2007 | Merade et al. | EP | 1159920 A2 | 12/2001 |
| 2007/0055094 | A1 | 3/2007 | Chen | EP | 1159921 | 12/2001 |
| 2007/0055095 | A1 | 3/2007 | Chu et al. | EP | 1239793 B1 | 9/2002 |
| 2007/0060788 | A1 | 3/2007 | Gellman | EP | 1239795 81 | 9/2002 |
| 2007/0062541 | A1 | 3/2007 | Zhou et al. | EP | 1342450 A1 | 9/2003 |
| 2007/0068538 | A1 | 3/2007 | Anderson et al. | EP | 1342454 A1 | 9/2003 |
| 2007/0078295 | A1 | 4/2007 | Landgrebe | EP | 1399082 B1 | 3/2004 |
| 2007/0088390 | A1 | 4/2007 | Paz et al. | EP | 1417934 A2 | 5/2004 |
| 2007/0089750 | A1 | 4/2007 | Astani et al. | EP | 1487377 A1 | 12/2004 |
| 2007/0089751 | A1 | 4/2007 | Astani et al. | EP | 1534154 | 6/2005 |
| 2007/0123746 | A1 | 5/2007 | MacLean | EP | 1549245 B1 | 7/2005 |
| 2007/0142698 | A1 | 6/2007 | Bourne et al. | EP | 1600118 A1 | 11/2005 |
| 2007/0156012 | A1 | 7/2007 | Tracey et al. | EP | 1609439 A1 | 12/2005 |
| 2007/0161849 | A1 | 7/2007 | Goldberg | EP | 1610714 A2 | 1/2006 |
| 2007/0203429 | A1 | 8/2007 | Ziv | EP | 1688105 A2 | 8/2006 |
| 2007/0225546 | A1 | 9/2007 | Anderson et al. | EP | 1909672 A2 | 4/2008 |
| 2007/0299299 | A1 | 12/2007 | Rosenblatt | EP | 1545285 B1 | 11/2010 |
| 2007/0299300 | A1 | 12/2007 | Smith et al. | EP | 1948073 A4 | 3/2011 |
| 2008/0004490 | A1 | 1/2008 | Bosley et al. | FR | 2712177 A1 | 5/1995 |
| 2008/0009665 | A1 | 1/2008 | Merade et al. | FR | 2785521 | 5/2000 |
| 2008/0009667 | A1 | 1/2008 | Longhini et al. | FR | 0102120 | 1/2002 |
| 2008/0009888 | A1 | 1/2008 | Ewers et al. | FR | 2852817 A1 | 10/2004 |
| 2008/0039678 | A1 | 2/2008 | Montpetit et al. | FR | 2859624 A1 | 3/2005 |
| 2008/0045782 | A1 | 2/2008 | Jimenez | FR | 2859901 A1 | 3/2005 |
| 2008/0082121 | A1 | 4/2008 | Chu | GB | 2382993 B | 6/2003 |
| 2008/0097329 | A1 | 4/2008 | Hodroff et al. | JP | 03070567 A | 3/1991 |
| 2008/0132753 | A1 | 6/2008 | Goddard | JP | 05161655 A | 6/1993 |
| 2008/0269547 | A1 | 10/2008 | Hortenstine | JP | 11221221 A | 8/1999 |
| 2008/0281148 | A1 | 11/2008 | Evans et al. | JP | 2002503510 A | 2/2002 |
| 2008/0300607 | A1 | 12/2008 | Meade et al. | JP | 2002143290 A | 5/2002 |
| 2009/0105743 | A1 | 4/2009 | Chu | JP | 2003501144 A | 1/2003 |
| 2009/0137862 | A1 | 5/2009 | Evans et al. | JP | 2003225240 A | 8/2003 |
| 2009/0149700 | A1 | 6/2009 | Garcia et al. | JP | 2005505313 A | 2/2005 |
| 2009/0221868 | A1 | 9/2009 | Evans | JP | 2005534422 A | 11/2005 |
| 2009/0306464 | A1 | 12/2009 | Griguol | JP | 4452180 B2 | 4/2010 |
| 2009/0318752 | A1 | 12/2009 | Evans et al. | SE | 503271 C2 | 4/1996 |
| 2010/0010501 | A2 | 1/2010 | Meade et al. | WO | 9003766 | 4/1990 |
| 2010/0030015 | A1 | 2/2010 | Delorme et al. | WO | 9003766 A1 | 4/1990 |
| 2010/0056856 | A1 | 3/2010 | Suslian et al. | WO | 9208412 A1 | 5/1992 |
| 2010/0197999 | A1 | 8/2010 | Deegan et al. | WO | 9310731 A1 | 6/1993 |
| 2010/0217069 | A1 | 8/2010 | Meade et al. | WO | 9315690 A2 | 8/1993 |
| 2010/0234679 | A1 | 9/2010 | Evans | WO | 9603091 A1 | 2/1996 |
| 2010/0241105 | A1 | 9/2010 | Meade et al. | WO | 9606567 | 3/1996 |
| 2011/0082328 | A1 | 4/2011 | Gozzi et al. | WO | 9606567 A1 | 3/1996 |
| 2011/0105833 | A1 | 5/2011 | Gozzi et al. | WO | 9606597 A1 | 3/1996 |
| 2011/0124954 | A1 | 5/2011 | Ogdahl et al. | WO | 9607355 A1 | 3/1996 |
| 2011/0282133 | A1 | 11/2011 | Anderson et al. | WO | 9608587 A1 | 3/1996 |
| 2012/0029488 | A1 | 2/2012 | Chu | WO | 9640307 A1 | 12/1996 |
| 2012/0108890 | A1 | 5/2012 | Evans | WO | 9713465 | 4/1997 |
| 2012/0116154 | A1 | 5/2012 | Evans et al. | WO | 9713465 A1 | 4/1997 |
| 2012/0253110 | A1 | 10/2012 | Evans et al. | WO | 9716121 | 5/1997 |
| | | | | WO | 9743982 A1 | 11/1997 |
| | | FOREIGN PATENT DOCUMENTS | | WO | 9831301 A1 | 7/1998 |
| | | | | WO | 9835632 | 8/1998 |
| DE | | 4220283 A1 | 12/1993 | WO | 9835632 A1 | 8/1998 |
| DE | | 4334419 A1 | 4/1995 | WO | 9922873 A1 | 5/1999 |
| DE | | 19544162 C1 | 4/1997 | WO | 9934744 A1 | 7/1999 |
| DE | | 10138950 A1 | 2/2003 | WO | 9942041 A1 | 8/1999 |
| DE | | 102 11 360 A1 | 10/2003 | WO | 9959477 A1 | 11/1999 |
| DE | | 10245076 A1 | 4/2004 | WO | 0018325 | 4/2000 |
| EP | | 0437481 A1 | 7/1991 | WO | 0027304 | 5/2000 |
| EP | | 0537769 A1 | 4/1993 | WO | 0027304 A1 | 5/2000 |
| EP | | 0556313 | 8/1993 | WO | 0040158 A2 | 7/2000 |
| EP | | 0557964 A1 | 9/1993 | WO | 0064370 A1 | 11/2000 |
| EP | | 0598976 A2 | 6/1994 | WO | 0066030 | 11/2000 |
| EP | | 0619984 A1 | 10/1994 | WO | 0074594 | 12/2000 |
| EP | | 0648474 A1 | 4/1995 | WO | 0074594 A1 | 12/2000 |
| EP | | 0668056 A1 | 8/1995 | WO | 0074613 | 12/2000 |
| EP | | 0692225 A2 | 1/1996 | WO | 0074613 A1 | 12/2000 |
| EP | | 0740925 | 11/1996 | WO | 0074633 | 12/2000 |
| EP | | 0745351 | 12/1996 | WO | 0106951 A1 | 2/2001 |
| EP | | 0774240 A1 | 5/1997 | WO | 0130246 | 5/2001 |
| EP | | 0778749 | 6/1997 | WO | 0147438 A1 | 7/2001 |
| EP | | 0854691 | 7/1998 | | | |

| | | |
|---|---|---|
| WO | 0152750 | 7/2001 |
| WO | 0180774 A1 | 11/2001 |
| WO | 0193656 A2 | 12/2001 |
| WO | 0202031 | 1/2002 |
| WO | 0202031 A1 | 1/2002 |
| WO | 0219945 A2 | 3/2002 |
| WO | 0219946 | 3/2002 |
| WO | 0226108 | 4/2002 |
| WO | 0228312 | 4/2002 |
| WO | 0228312 A1 | 4/2002 |
| WO | 0228315 | 4/2002 |
| WO | 0232284 A2 | 4/2002 |
| WO | 0238079 A2 | 5/2002 |
| WO | 0239890 A2 | 5/2002 |
| WO | 0239914 | 5/2002 |
| WO | 02058562 | 8/2002 |
| WO | 02058562 A1 | 8/2002 |
| WO | 02058563 A1 | 8/2002 |
| WO | 02058564 | 8/2002 |
| WO | 02058565 | 8/2002 |
| WO | 02058565 A2 | 8/2002 |
| WO | 02062237 | 8/2002 |
| WO | 02065921 | 8/2002 |
| WO | 02065922 | 8/2002 |
| WO | 02065923 | 8/2002 |
| WO | 02065923 A1 | 8/2002 |
| WO | 02069781 A2 | 9/2002 |
| WO | 02071931 | 9/2002 |
| WO | 02071931 A1 | 9/2002 |
| WO | 02078548 A1 | 10/2002 |
| WO | 02098322 | 12/2002 |
| WO | 02098322 A1 | 12/2002 |
| WO | 03002027 | 1/2003 |
| WO | 03002027 A1 | 1/2003 |
| WO | 03013369 | 2/2003 |
| WO | 03028585 A2 | 4/2003 |
| WO | 03037215 A2 | 5/2003 |
| WO | 03053252 A1 | 7/2003 |
| WO | 03068107 | 8/2003 |
| WO | 03068107 A1 | 8/2003 |
| WO | 03073960 A1 | 9/2003 |
| WO | 03075792 | 9/2003 |
| WO | 03086205 A2 | 10/2003 |
| WO | 03092546 | 11/2003 |
| WO | 03096928 | 11/2003 |
| WO | 03096929 A1 | 11/2003 |
| WO | 03096930 | 11/2003 |
| WO | 03096930 A1 | 11/2003 |
| WO | 03101344 A1 | 12/2003 |
| WO | 2004004600 A1 | 1/2004 |
| WO | 2004008977 A1 | 1/2004 |
| WO | 2004012579 A2 | 2/2004 |
| WO | 2004012626 A1 | 2/2004 |
| WO | 2004016196 A2 | 2/2004 |
| WO | 2004017862 A2 | 3/2004 |
| WO | 2004019786 | 3/2004 |
| WO | 2004034912 A1 | 4/2004 |
| WO | 2004056273 A1 | 7/2004 |
| WO | 2004086983 A1 | 10/2004 |
| WO | 2004091442 A2 | 10/2004 |
| WO | 2004098461 A2 | 11/2004 |
| WO | 2005037132 A2 | 4/2005 |
| WO | 2005087153 A2 | 9/2005 |
| WO | 2005094741 A1 | 10/2005 |
| WO | 2005110273 A1 | 11/2005 |
| WO | 2005110274 A2 | 11/2005 |
| WO | 2005112842 A1 | 12/2005 |
| WO | 2005122954 A1 | 12/2005 |
| WO | 2006040307 A1 | 4/2006 |
| WO | 2006045042 A1 | 4/2006 |
| WO | 2006046950 A1 | 5/2006 |
| WO | 2006069078 A2 | 6/2006 |
| WO | 2006081545 | 8/2006 |
| WO | 2006084165 A2 | 8/2006 |
| WO | 2006084166 A2 | 8/2006 |
| WO | 2006108145 A1 | 10/2006 |
| WO | 2006108964 A2 | 10/2006 |
| WO | 2007013465 A1 | 2/2007 |
| WO | 2007059199 A2 | 5/2007 |
| WO | 2007087190 A2 | 8/2007 |
| WO | 2007097994 A2 | 8/2007 |
| WO | 2007149348 A2 | 12/2007 |
| WO | 2008065467 A1 | 6/2008 |
| WO | 2009064866 A1 | 5/2009 |

OTHER PUBLICATIONS

Delorme, Emmanuel., "Transobturator urethral suspension: mini-invasive procedure in the treatment of stress urinary incontinence in women," Progress in Urology, 11(6):1306-13, Dec. 2001.

Ghoniem, Gamal et al., "Modified Pubovaginal Sling and Martius Graft for Report of the Recurrent Vesicovaginal Fistula Involving the Internal Urinary Sphincter," Eur Urol 1995; 27:241-245.

Gormley, E. Ann et al., "Pubovaginal slings for the management of urinary incontinence in female adolescents," The Journal of Urology, vol. 152, pp. 822-825, Aug. 1994.

Kelly, Mark J. et al., "Symptom analysis of patients undergoing modified Pereyra bladder neck suspension for urinary stress incontinence," Urology, vol. 37, No. 3, Mar. 1991.

Kersey, J., "The guaze hammock sling operation in the treatment of stress incontinence," British Journal of Obstetrics and Gynaecology, vol. 90, pp. 945-949, Oct. 1983.

Kil, P.J.M. et al., "Transvaginal ultrasonography and urodynamic evaluation after suspension operations: comparison among the Gittes, Stamey and Burch suspensions," The Journal of Urology, vol. 146, pp. 132-136, Jul. 1991.

Korman, Howard J. et al., "Success rate of modified Pereyra bladder neck suspension determined by outcomes analysis," The Journal of Urology, vol. 152, pp. 1453-1457, Nov. 1994.

Parra, O. et al., "Experience with a Simplified Technique for the Treatment of Female Urinary Incontinence," The British Journal of Urology (1990), 66, 615-617.

PCT/US07/78308 filed Sep. 12, 2007 International Search Report dated Jun. 5, 2008.

PCT/US07/78308 filed Sep. 12, 2007 Written Opinion dated Jun. 5, 2008.

Petros, Peter E. Papa et al., "The Combined Intravaginal Sling and Tuck Operation. An Ambulatory Procedure for Cure of Stress and Urge Incontinence," Acta Obstet Gynecol Scan Suppl 153: 53, pp. 115-117, 1990.

Raz, Shlomo et al., "The Raz Bladder Neck Suspension: Results in 206 Patients," The Journal of Urology, vol. 148, pp. 845-850, Sep. 1992.

Ulmsten, U. et al., "An Ambulatory Surgical Procedure Under Local Anesthesia for Treatment of Female Urinary Incontinence," Int Urogynecol J (1996) 7:81-86.

Wahle, Gregory R. et al., "Vaginal Surgery for Stress Urinary Incontinence," Urology, vol. 43, No. 4, pp. 416-419, Apr. 1994.

EP 06800736.8 filed Aug. 3, 2006 Search Report dated Apr. 26, 2010.

EP 06824802.0 filed Aug. 3, 2006 Search Report dated Dec. 13, 2010.

EP 06827826.6 filed May 14, 2008 Supplementary Search Report dated Feb. 4, 2011.

EP 06846828.9 filed Dec. 28, 2006 Office Action dated May 18, 2010.

EP 06846828.9 filed Dec. 28, 2006 Official Minutes dated Oct. 12, 2012.

EP 06846828.9 filed Dec. 28, 2006 Search Report dated Apr. 26, 2010.

EP 07753112.7 filed Mar. 15, 2007 Supplemental European Search Report dated Dec. 30, 2010.

Falconer, C., Ekman-Ordeberg, G., Malmstrom, A., Ulmsten, U.; "Clinical Outcome and Changes in Connective Tissue Metabolism After Intravaginal Slingplasty in Stress Incontinent Women"; The International Urogynecology Journal; vol. 7, pp. 133-137, 1996.

Falconer, C., Soderberg, M., Blomgren, B., Ulmsten, U.; "Influence of Different Sling Materials on Connective Tissue Metabolism in Stress Urinary Incontinent Women"; The International Urogynecology Journal; S19-S23, 2001.

Glowacki, CA, et al., "Bone anchors in urogynecology," Clin Obstet Gynecol, Sep. 2000;43(3):659-69, Review.

Gomelsky, Alex, et al., "Biocompatibility Assessment of Synthetic Sling Materials for Female Stress Urinary Incontinence," The Journal of Urology, Oct. 2007, vol. 178, pp. 1171-1181.

Horbach, Nicolette S.; "Suburethral Sling Procedures"; Urogynecology and Urodynamics Theory and Practice Fourth Edition; Chapter 42, pp. 569-579, 1996.

Image, <http://www.ivstunneller.com/images/anterior-procedure.jpg>printed on Jul. 10, 2006.

Image, www.obgyn.neUurogyn/articles/moore_cystocele , printed Jul. 10, 2006 and Mar. 10, 2011, <http://www.obgyn.neUurogyn/articles/moore_cystocele>.

Iosif, S., et al., "Urodynamic studies of women with prolapse and stress incontinence before and after surgical repair," Urodynamics Studies, 101:1433-1442 (1979).

Jacquetin B., "Bladder suspension exclusively through the vagina: at last!" J Gynecol Obstet Biol Reprod 1991;20(8):1143-4, Paris.

Jacquetin B., "Genital prolapses. Diagnosis," Rev Prat. Sep. 15, 2001;51(14):1609-16.

Jacquetin B., "Use of "TVT" in surgery for female urinary incontinence," J Gynecol Obstet Biol Reprod, May 2000;29(3):242-7.

Johnson & Johnson (Article), "Gynecare Prolift Systems: 'You Know Where You Want to Go . . . GPS for Pelvic Floor Repair,'" <http://www.jnjgateway.com/home.jhtml?loc=USENG&page=viewContent&contentId=09008b98>8102f39b&parentId=09008b988102f39b (2006).

Johnson & Johnson Gateway®, "Optimal technique for access to anatomic landmarks," <http://www.jnjgateway.com/home.jhtml?loc=USENG&page=viewContent&contentID=090> (2005).

Johnson & Johnson Gateway®: Gynecare Prolift Innovative Design, http://www.jnjgateway.com/home.jhtml?loc=USENG&page=viewContent&contentID=090 (2005).

Johnson & Johnson Gateway®: Gynecare TVT Abdominal Approach, <http://www.jnjgateway.com/home.jhtml?loc=USENG&page.=vieewContent&contentID=090> (2005).

Johnson & Johnson Gateway®: Gynecare TVT Obturator System, "Tension-Free Support for Incontinence" <http://www.jnjgateway.com/home.jhtml?loc=USENG&page=viewContent&contentID=090> (2005).

Johnson & Johnson Gateway®: Vaginal Approach, <http://www.jnjgateway.com/home.jhtml?loc=USENG&page=viewContent&contentID=090> (2005).

JP 2008-525210 filed Feb. 1, 2008 Office Action dated Oct. 5, 2011.

JP 2008-525211 filed Feb. 1, 2008 Office Action dated Oct. 31, 2011.

JP 2008-525252 filed Aug. 3, 2006 Office Action dated Aug. 26, 2011.

JP 2008-525252 filed Aug. 3, 2006 Office Action dated May 11, 2012.

JP 2008-548841 filed Jun. 27, 2008 Office Action dated Jan. 19, 2012.

Karlovsky, Matthew E., et al., "Surgical Treatment of Stress Urinary Incontinence", Journal of Urology, 2003.

Karmarkar, Santoshi J., et al., "The 3-loop technique: A reliable technique for anterior pubic fixation in bladder exstrophy," The Journal of Urology, Sep. 1995 vol. 154, 1173-1176.

Karram, Mickey M ., Bhatia, Narender N.; "Patch procedure: Modified Transvaginal Fascia Lata Sling for recurrent or severe stress urinary incontinence"; Obstetrics and Gynecology, pp. 461-463, Mar. 1990.

Kobashi, Kathleen C., et al., "Erosion of Woven Polyester Pubovaginal Sling," The Journal of Urology, Dec. 1999, vol. 162, pp. 2070-2072.

Korda, Andrew; Peat, Brian; Hunter, Peter; "Experience with Silastic Slings for Female Urinary Incontinence"; Aust NZ J Obstet Gynaecol, pp. 150-154, 1989.

Lichtenstein, Irving L, Shulman, Alex G., Amid, Parviz K., Montllor, Michele M.; "The Tension-Free Hernioplasty"; The American Journal of Surgery, vol. 157; Feb. 1989.

McIndoe, G.A.J., Jones, R.W., Grieve B.W.; "The Aldridge Sling Procedure in the Treatment of Urinary Stress Incontinence"; Aust NZ J Obstet Gynaecol; 1987.

MedlinePlus Medical Encyclopedia, "Female urinary tract," http://www.nlm.nih.gov/medlineplus/ency/imagepages/1122.htm (2004).

Miklos et al., Laparoscopic Urogynecology Center of Atlanta—Dr. Miklos & Dr. Moore, "Laparoscopic and Minimally Invasive Procedures, 'Tension Free Vaginal Tape (TVT) Sling'" printed Jul. 12, 2006; <http://www.urogynecologychannel.net/lap_proc12.php>.

Miklos et al., Vaginal prolapse relaxation and enterocele repair, printed Jul. 12, 2006; http://www.urogynecologychannel.net/prolapse6.php.

Miklos et al., Vaginal prolapse relaxation, posterior vaginal wall prolapse, printed Jul. 12, 2006; http://www.urogynecologychannel.net/prolapse3.php.

Miklos et al., Vaginal prolapse relaxation, uterine prolapse, printed Jul. 12, 2006; <http://www.urogynecologychannel.net/prolapse4.php>.

Miklos et al., Vaginal prolapse relaxation, uterosacral ligaments, printed Jul. 12, 2006; http://www.urogynecologychannel>.net/prolapse2a.php.

Miklos et al., Vaginal prolapse relaxation, vaginal vault prolapse, printed Jul. 12, 2006; <http://www.urogynecologychannel.net/prolapse5.php>.

Miklos et al., Vaginal relaxation, vaginal prolapse relaxaton, enterocele repair, Types of Vaginal Prolapse, printed on Jul. 12, 2006, http://www.urogyneocologychannel.net/prolapse.php?id=Prolapse.

Moore, Robert D., "Transobturator Approach for Cystocele Repair With Anterior Wall Mesh," <http://www.obgyn.net/hysterectomy-alternatives/hysterectomy-alternatives.asp>? page=urogyn/articles/moore_cystocele (2006).

Morgan, J.E.; "A sling operation, using Marlex polypropylene mesh, for treatment of recurrent strss incontinence." vol. 106, No. 3, pp. 369-377, Feb. 1970.

Mubiayi N., et al., "Surgical cure of stress urinary incontinence with vaginal tissue sling: technique, results, indications," Prog Urol. Feb. 2002;12(1):60-9.

Narik, G., Palmrich, A.H.; "A simplified sling operation suitable for routine use"; American Journal of Obstetrics & Gynecology, vol. 84, No. 3, Aug. 1962.

Netterimages.com, "Cystocele, Urethrocele," Image No. 5192, printed Jul. 24, 2006; <http://ww.netterimages.com/images/vpv/000/000/005/5192-05> . . . .

Netterimages.com, "Rectocele, Enterocele," Image No. 5193, printed Jul. 24, 2006; <http://www.netterimages.com/image/5193.htm>.

Nguyen, JK, "Current concepts in the diagnosis and surgical repair of anterior vaginal prolapse due to paravaginal defects," Obstet Gynecol Surv, Apr. 2001;56(4):239-46.

Nichols, David H.; "The Mersilene Mesh Gauze-Hammock for Severe Urinary Stress Incontinence"; Obstetrics and Gynecology; Obstetrics & Gynegology, vol. 41, No. 1, pp. 88-93, Jan. 1973.

Nickel, RF, et al, "Evaluation of a transpelvic sling procedure with and without colposuspension for treatment of female dogs with refractory urethral sphincter mechanism incompetence." Vet Surg. Mar.-Apr. 1998;27(2):94-104.

Norris, Jeffrey P., Breslin, David S., Staskin, David R.; "Use of Synthetic Material in Sling Surgery: A Minimally Invasive Approach", Journal of Endourology; vol. 10, No. 3, Jun. 1996.

O'Donnell, Pat D.; "Combined Raz Urethral Suspension and McGuire Pubovaginal Sling for Treatment of Complicated Stress Urinary Incontinence"; Journal of the Arkansas Medical Society, vol. 88, No. 8, pp. 389-392, Jan. 1992.

Okoshi, Takafumi, et al., "Long-term Results of a New Antithrombogenic Cardiac Wall Substitute," Trans Am Soc. Artif Intern Organs, XXXV:391-395 (1989).

PCT/AU2000/001298 filed Oct. 20, 2000 International Preliminary Examination Report dated Jan. 29, 2002.

PCT/AU2000/001298 filed Oct. 20, 2000 Search Report dated Jan. 3, 2001.

PCT/US03/24212 filed Aug. 1, 2003 International Search Report dated May 28, 2004.

PCT/US03/24212 filed Aug. 1, 2003 Written Opinion dated Aug. 24, 2004.

PCT/US2003/013113 filed Apr. 28, 2003 International Preliminary Examination Report dated Oct. 14, 2004.

PCT/US2003/013113 filed Apr. 28, 2003 International Seach Report dated Oct. 15, 2003.

PCT/US2003/024212 filed Aug. 1, 2003 International Search Report dated May 24, 2004.

PCT/US2003/024212 filed Aug. 1, 2003 Written Opinion dated Aug. 24, 2004.
PCT/US2006/030369 filed Aug. 3, 2006 International Preliminary Report on Patentability dated Mar. 31, 2009.
PCT/US2006/030369 filed Aug. 3, 2006 Search Report dated Aug. 12, 2008.
PCT/US2006/030369 filed Aug. 3, 2006 Written Opinion dated Aug. 12, 2008.
PCT/US2006/030370 filed Aug. 3, 2006 International Preliminary Report on Patentability dated Feb. 4, 2008.
PCT/US2006/030370 filed Aug. 3, 2006 Search Report dated Jul. 20, 2007.
PCT/US2006/030370 filed Aug. 3, 2006 Written Opinion dated Jul. 20, 2007.
PCT/US2006/030581 filed Aug. 3, 2006 International Preliminary Report on Patentability dated Mar. 17, 2009.
PCT/US2006/030581 filed Aug. 3, 2006 Search Report dated Jul. 7, 2008.
PCT/US2006/030581 filed Aug. 3, 2006 Written Opinion dated Jul. 7, 2008.
PCT/US2006/044315 filed Nov. 14, 2006 International Preliminary Report on Patentability dated Mar. 24, 2009.
PCT/US2006/044315 filed Nov. 14, 2006 International Seach Report dated May 6, 2008.
PCT/US2006/044315 filed Nov. 14, 2006 Written Opinion dated May 6, 2008.
PCT/US2006/062639 filed Dec. 28, 2006 International Preliminary Report on Patentability dated Oct. 7, 2008.
PCT/US2006/062639 filed Dec. 28, 2006 Search Report dated Oct. 1, 2007.
PCT/US2006/062639 filed Dec. 28, 2006 Written Opinion dated Oct. 1, 2007.
PCT/US2007/006461 filed on Mar. 15, 2007 International Preliminary Report on Patentability dated Sep. 16, 2008.
PCT/US2007/006461 filed on Mar. 15, 2007 Search Report dated May 22, 2008.
PCT/US2007/006461 filed on Mar. 15, 2007 Written Opinion dated May 22, 2008.
PCT/US2008/083381 filed Nov. 13, 2008 International Search Report dated Dec. 29, 2008.
PCT/US2008/083381 filed Nov. 13, 2008 Written Opinion of the International Searching Authority dated Dec. 29, 2008.
Pelosi, Ma, et al., "The transobturator sling: newest tension-free suburethral sling for treatment of stress urinary incontinence," Surg Technol Int. 2004;13:173-9. Review.
Petros, Peter E. Papa, "Ambulatory surgery for urinary incontinence and vaginal prolapse," Med. J. of Australia, 161:171-172 (1994).
Raz, Shlomo; Female Urology; Second Edition; Selected Chapters, © 1996.
Ridley, John H.; "Appraisal of the Goebell-Frangenheim-Stoeckel sling procedure"; American Journal of Obstetrics & Gynecology, vol. 95, No. 5, pp. 714-721, Jul. 1966.
Scotti, RJ, et al., "Paravaginal repair of lateral vaginal wall defects by fixation to the ischial periosteum and obturator membrane," Am J Obstet Gynecol. Dec. 1998;179(6 Pt 1):1436-45.
Shands Healthcare, "Bladder neck is elevated by stitching it and the urethra to anterior pubic bone," Copyright 1997-2011, printed Nov. 3, 2010,<http://www.shands.org/health/imagepages/17202.htm>.
Silver, Richard I., et al., "Staged closure of the pelvis in cloacal exstrophy: first description of a new approach," The Journal of Urology, Jan. 1999, vol. 161, pp. 263-266.
Stanton, Stuart L.; "Suprapubic Approaches for Stress Incontinence in Women"; Journal of the American Geriatrics Society, vol. 38, No. 3, pp. 348-351, Mar. 1990.
Staskin, David R., Choe, Jong M., Breslin, David S.; "The Gore-Tex sling procedure for female sphincteric incontinence: indications, technique, and results"; World J. Urol.; vol. 15, pp. 295-299, 1997.
Sussman, J.S., et al., "A Comparison of Methods of Repairing the Symphysis Pubis in Bladder Exstrophy by Tensile Testing," Brit. J. Urol., 79: 979-984, 1997.
U.S. Appl. No. 10/633,254, filed Aug. 1, 2003 Advisory Action dated Aug. 26, 2008.
U.S. Appl. No. 10/633,254, filed Aug. 1, 2003 Decision on Appeal dated Jul. 20, 2011.
U.S. Appl. No. 10/633,254, filed Aug. 1, 2003 Final Office Action dated Jun. 18, 2008.
U.S. Appl. No. 10/633,254, filed Aug. 1, 2003 Non-Final Office Action dated Jan. 29, 2007.
U.S. Appl. No. 10/633,254, filed Aug. 1, 2003 Non-Final Office Action dated Nov. 15, 2005.
U.S. Appl. No. 10/633,254, filed Aug. 1, 2003 Non-Final Office Action dated Sep. 18, 2007.
U.S. Appl. No. 10/633,254, filed Aug. 1, 2003 Notice of Allowance dated Oct. 11, 2011.
U.S. Appl. No. 11/993,003, filed Jan. 22, 2008 Examiner's Answer dated Nov. 30, 2011.
U.S. Appl. No. 11/993,003, filed Jan. 22, 2008 Non-Final Office Action dated Jul. 20, 2011.
U.S. Appl. No. 11/993,089, filed Jun. 9, 2010 Non-Final Office Action dated Aug. 27, 2012.
U.S. Appl. No. 11/993,375, filed Feb. 6, 2009 Non-Final Office Action dated May 10, 2011.
U.S. Appl. No. 11/993,003, filed Jan. 22, 2008 Advisory Action dated Feb. 8, 2011.
U.S. Appl. No. 11/993,003, filed Jan. 22, 2008 Final Office Action dated Dec. 10, 2010.
U.S. Appl. No. 11/993,003, filed Jan. 22, 2008 Non-Final Office Action dated Jul. 14, 2010.
U.S. Appl. No. 12/093,493, filed Jul. 14, 2008 Final Office Action dated Jul. 6, 2011.
U.S. Appl. No. 12/093,493, filed Jul. 14, 2008 Non-Final Office Action dated Jan. 20, 2011.
U.S. Appl. No. 12/093,493, filed Jul. 14, 2008 Notice of Allowability dated Sep. 22, 2011.
U.S. Appl. No. 12/159,589, filed Aug. 15, 2008 Examiner's Answer dated Nov. 9, 2011.
U.S. Appl. No. 12/159,589, filed Aug. 15, 2008 Final Office Action dated May 12, 2011.
U.S. Appl. No. 12/159,589, filed Aug. 15, 2008 Non-Final Office Action dated Dec. 10, 2010.
U.S. Appl. No. 12/159,589, filed Aug. 15, 2008 Non-Final Office Action dated Jul. 12, 2010.
U.S. Appl. No. 12/159,589, filed Aug. 15, 2008 Notice of Panel Decision dated Aug. 29, 2011.
U.S. Appl. No. 12/269,749, filed Nov. 12, 2008 Non-Final Office Action dated Sep. 14, 2011.
U.S. Appl. No. 12/269,749, filed Nov. 12, 2008 Notice of Allowance dated Mar. 16, 2012.
U.S. Appl. No. 12/282,641, filed Dec. 4, 2008 Non-Final Office Action dated Dec. 8, 2011.
U.S. Appl. No. 12/282,641, filed Dec. 4, 2008 Non-Final Office Action dated Jul. 12, 2012.
Wall, LL, et al., Use of a pedicled rectus abdominus muscle flap sling in the treatment of complicated stress urinary incontinence. Am J Obstet Gynecol. Dec. 1996;175(6):1460-4; Discussion 1464-6.
Walters, Mark D., et al., "Anterior vaginal wall prolapse: Innovative surgical approaches," Cleveland Clinic Journal of Medicine, Dec. 2005, 72:4 S20-S27.
Yan, A., et al, "Cystocele repair by a synthetic vaginal mesh secured anteriorly through the obturator foramen," Eur J Obstet Gynecol Reprod Biol, Jul. 15, 2004;115(1):90-4.
Zimmern, Philippe, et al., "A prospective evaluation of four-corner bladder neck suspension for grade II/III cystocele repair," Urodynamics Soc. Symp. Abstracts, p. 231 (1990).
AU 2006332514 filed Dec. 28, 2006 First Examiner's Report dated Oct. 4, 2011.
AU 2006332514 filed Dec. 28, 2006 Second Examiner's Report dated Jul. 5, 2012.
Bard (Article), "Avaulta™ BioSynthetic Support System," http://www.crbard.com/news/innovations/Avaulta.cfm (2007).
Bard (Article), "AVAULT™ BioSynthetic Support System 'Anterior and Posterior Posterior Pelvic Floor Defect Repair with the Avaulta™ Bio-synthetic Support system,'" http://www.bardmdu.com/products/loadProduct.aspx?prodID=280&bUnitID=3 (2007).

Bard (Article), "PelviLace® TO Trans-Obturator BioUrethral Support System," http://www.bardurological.com/products/loadproduct.aspx?prodID=277 (2008).

Bard (Article), "URETEX® TO—Trans-Obturator Urethral Support System 'Not all Mesh is created equal,'" Copyright 1997-2004, <http://www.bardurological.com/products/loadproductaspx?prodID=186>.

Bard Photo Library "Uretex® Mesh," printed Jul. 12, 2006; http://www.bardurological.com/products/product_photoLibrary.aspx?prodID=185&photoID=269.

Bard Photo Library, "Avaulta™ Posterior BioSynthetic Support System", Copyright 1997-2008; printed Oct. 23, 2008; http://www.bardurological.com/products/product_photoLibrary.aspx?prodID=281&photoID=326>.

Bard Photo Library, Uretex® Mesh in the Anatomy—printed Jul. 12, 2006 <http://www.bardurological.com/products/product_photoLibrary.aspx?prodID=185&photoID=270>.

Bard Photo Library, Hook Introducer 2 printed Jul. 12, 2006 <http://www.bardurological.com/products/product_photoLibrary.aspx?prodID=186&photoID=344>.

Bard Photo Library, Hook Introducer printed Jul. 12, 2006 http://www.bardurological.com/products/product_photoLibrary.aspx?prodID=186&photoID=343.

Bard Photo Library, Pelvic Diagram 1 (photo id 282) printed Jul. 12, 2006 http://www.bardurological.com/products/product_photoLibrary.aspx?prodID=186&photoID=282.

Bard Photo Library, Pelvic Diagram 2 (photo id 283) printed Jul. 12, 2006 http://www.bardurological.com/products/product_photoLibrary.aspx?prodID=186&photoID=283.

Bard Photo Library, Pelvic Diagram 3 (photo id 284) printed Jul. 12, 2006 http://www.bardurological.com/products/product_photoLibrary.aspx?prodID=186&photoID=284.

Bard Photo Library, Pelvic Diagram 4 (photo id 285) printed Jul. 12, 2006 http://www.bardurological.com/products/product_photoLibrary.aspx?prodID=186&photoID=285.

Bard Photo Library, Surgical Technique (photo id 336) printed Jul. 12, 2006 http://www.bardurological.com/products/product_photoLibrary.aspx?prodID=186&photoID=336.

Bard Photo Library, Surgical Techniques (photo id 337) printed on Jul. 12, 2006 http://www.bardurological.com/products/product_photoLibrary.aspx?prodID=186&photoID=337.

Bard Photo Library, Surgical Techniques (photo id 338) printed Jul. 12, 2006 http://www.bardurological.com/products/product_photoLibrary.aspx?prodID=186&photoID=338.

Bard Photo Library, Surgical Techniques (photo id 339) printed Jul. 12, 2006 http://www.bardurological.com/products/product_photoLibrary.aspx?prodID=186&photoID=339.

Bard Photo Library, Surgical Techniques (photo id 340) printed Jul. 12, 2006 http://www.bardurological.com/products/product_photoLibrary.aspx?prodID=186&photoID=340.

Bard Photo Library, Surgical Techniques (photo id 341) printed Jul. 12, 2006 http://www.bardurological.com/products/product_photoLibrary.aspx?prodID=186&photoID=341.

Bard Photo Library, Surgical Techniques (photo id 345) printed Jul. 12, 2006 http://www.bardurological.com/products/product_photoLibrary.aspx?prodID=186&photoID=345.

Bard Photo Library, Uretex T.O. Transobturator Urethral Support System printed Jul. 12, 2006 <http://www.bardurological.com/products/product_photoLibrary.aspx?prodID=186&photoID=266>.

Bard Photo Library, Uretex® TO Trans-Obturator Urethral Support System dated Oct. 23, 2008<http://www.bardurological.com/products/product_photoLibrary.aspx?prodID=186&photoID=204&bUnitID=2>.

Bard Photo Library, Urethral Mesh printed Jul. 12, 2006 <http://www.bardurological.com/products/product_photoLibrary.aspx?prodID=185&photoID=271>.

Bard, "Avaulta™ Anterior BioSynthetic Support System," Copyright 2006-2011, http://www.bardnordic.com/main/product.asp?.sectionTypeID=2&sectionID=6&productID=247.

Bard, "Uretex® Self-Anchoring Urethral Support System—FAQ," printed Jul. 12, 2006; <http://www.bardurological.com/products/product_faq.aspx?prodID=185>.

Bryans, Fred E. "Marlex gauze hammock sling operation with Cooper's ligament attachment in the management of recurrent urinary stress incontinence." American Journal of Obstetrics and Gynecology, vol. 133, No. 3, Feb. 1979.

Burch, John C., "Urethrovaginal fixation to Cooper's ligament for correction of stress incontinence, cystocele, and prolapse," Am. J. Obst. & Gyne, 281-290 (1961).

Burch, John C.; "Urethrovaginal fixation to Cooper's ligament for correction of stress incontinence, cystocele, and prolapse." American Journal of Obstetrics & Gynecology, vol. 31, No. 2, Feb. 1961, pp. 281-290.

Choe, JM, "Preventing urethral obstruction using the 6-point fixation and weight-adjusted spacing nomogram during sling surgery," Int Urogynecol J Pelvic Floor Dysfunct, 2001;12(2):122-8.

Choe, Jong M., Staskin, David R.; "Gore-Tex Patch Sling: 7 Years Later"; Adult Urology, 54(4), pp. 641-646, 1999.

CN 200880115957.3 filed May 12, 2010 Office Action dated Apr. 28, 2012.

Collinet, P., et al., "Cure de cystocele par plastron vaginal," J Gynecol Obstet Biol Reprod, 29:197-201 (2000).

Cook; Urogynecology; Product Technical Datasheet and Order form. 1996.

Cosson, M., et al., "Cure of cystocele with vaginal patch," Prog Urol. Apr. 2001;11(2):340-6.

Cosson, M., et al., "The vaginal patch plastron for vaginal cure of cystocele. Preliminary results for 47 patients," Eur J Obstet Gynecol Reprod Giol. Mar. 2001;95(1):73-80.

Cosson, Michel, et al., "Cure de cystocele par plastron vaginal," Progres en Urologie, 11:340-346 (2001).

Cruikshank, Stephen H., et al., "Anterior vaginal wall culdeplasty at vaginal hysterectomy to prevent posthysterectomy anterior vaginal wall prolapse," Am. J. Obstet. Gynecol., 1863-1872 (1996).

De Leval J., "Novel surgical technique for the treatment of female stress urinary incontinence: transobturator vaginal tape inside-out," Eur Urol. Dec. 2003;44(6):724-30.

Delorme, E., "Transobturator urethral suspension: mini-invasive procedure in the treatment of stress urinary incontinence in women," Prog Urol. Dec. 2001;11(6):1306-13.

Delorme, E., et al., "Transobturator tape (Uratape). A new minimally invasive method in the treatment of urinary incontinence in women," Prog Urol. Sep. 2003;13(4):656-9.

Di Benedetto, V., et al., "Transurethral Puncture of Ureterocele Associated With Single Collecting System in Neonates," J. Ped. Surg., 32: 1325-1327, 1997.

Dmochowski et al., "Biocompatibility Assessment of Synthetic Sling Materials for Female Stress Urinary Incontinence," The Journal of Urology, vol. 178, Issue 4, pp. 1171-1181, Oct. 2007.

Dmochowski et al., "Erosion of Woven Polyester Pubovaginal Sling," The Journal of Urology, vol. 162, Issue 6, pp. 2070-2072, Dec. 1999.

Dmochowski, R., et al., "The Protegen Sling for the Treatment of Female Stress Urinary Incontinence," J. Urol., http://home.satx.rr.com/sgsu/usurg/protegen.html (1997).

Eglin, G., et al., "Transobturator subvesical mesh. Tolerance and short-term results of a 103 case continuous series," Gynecology Obstetrique & Fertilite, Jan. 2003;31(1):14-19(6).

EP 03751825.5 Supplementary European Search Report dated Jun. 19, 2009.

EP 06789465.9 filed Aug. 3, 2006 Search Report dated Apr. 28, 2010.

EP 06800736.8 filed Aug. 3, 2006 Examination Report dated Feb. 24, 2012.

EP 08849041.2 extended European Search Report dated Mar. 12, 2013.

MX/a/2010/005271 Office Action dated Mar. 7, 2013.

U.S. Appl. No. 13/524,408, filed Jun. 15, 2012 Non-Final Office Action dated Mar. 7, 2013.

Walters, Mark D., Percutaneous Suburethral Slings: State of the Art, presented at the conference of the American Urogynecologic Society, Chicago (Oct. 2001).

* cited by examiner

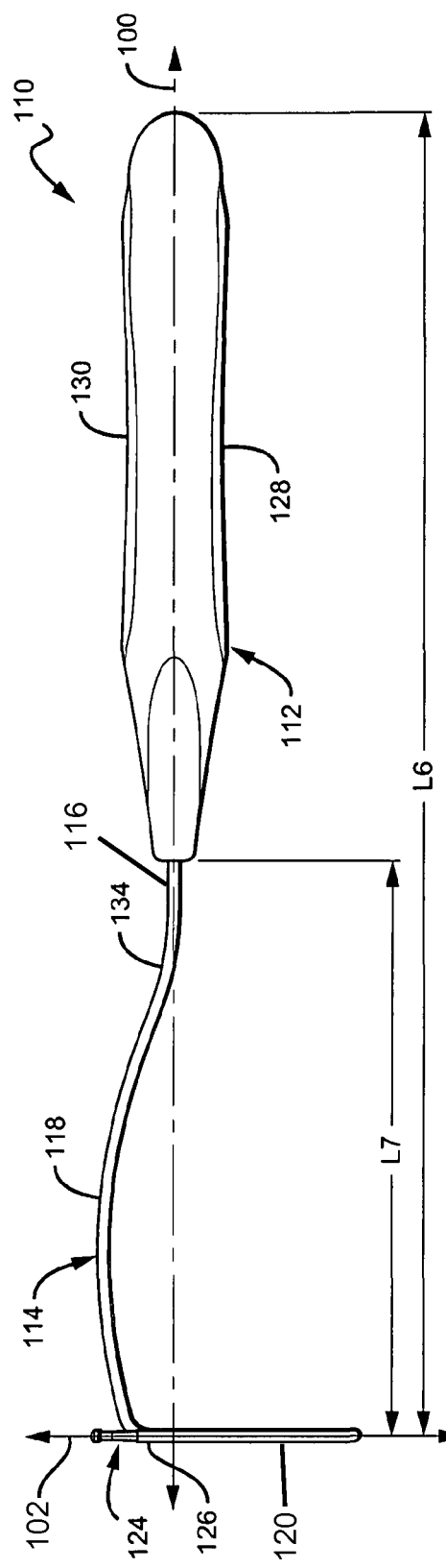
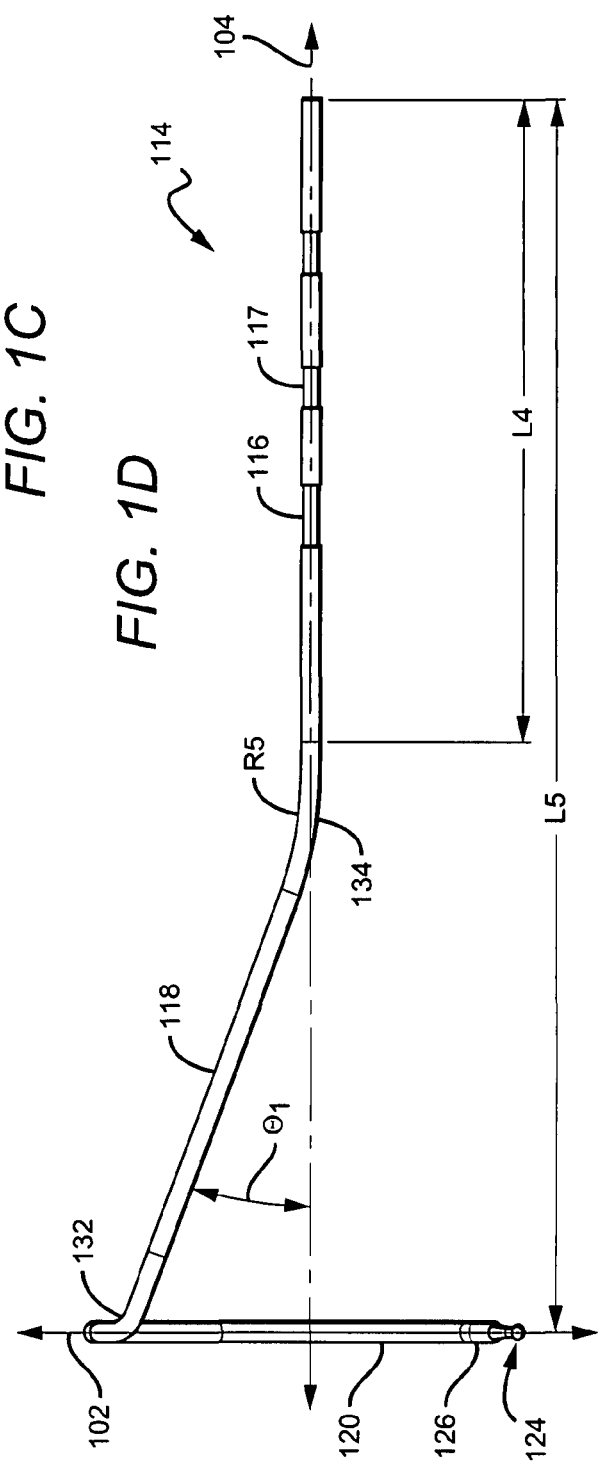
FIG. 1C
FIG. 1D

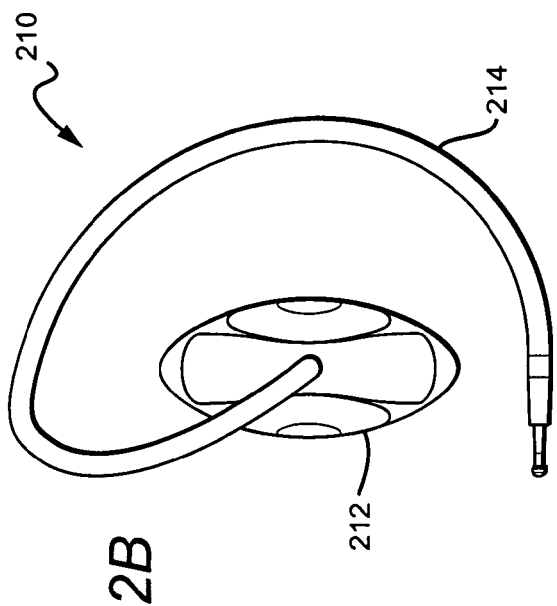
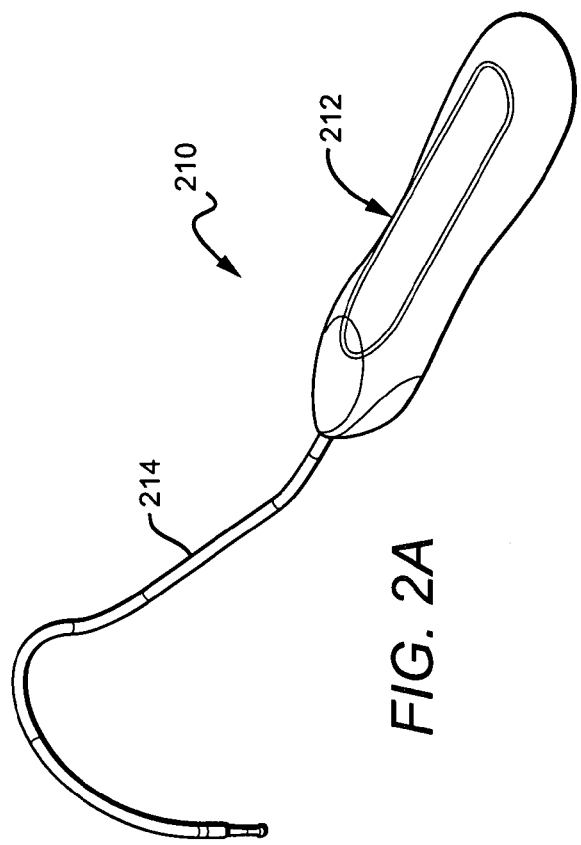
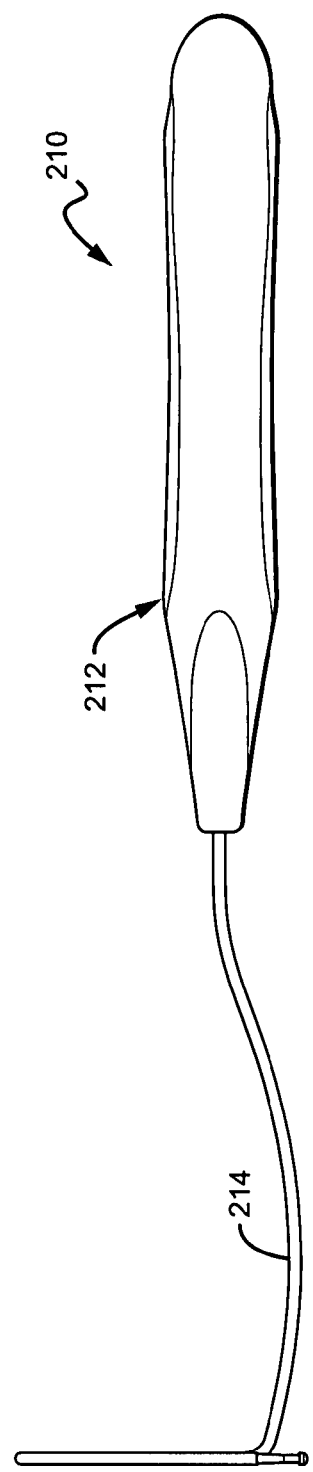
FIG. 2A
FIG. 2B
FIG. 2C

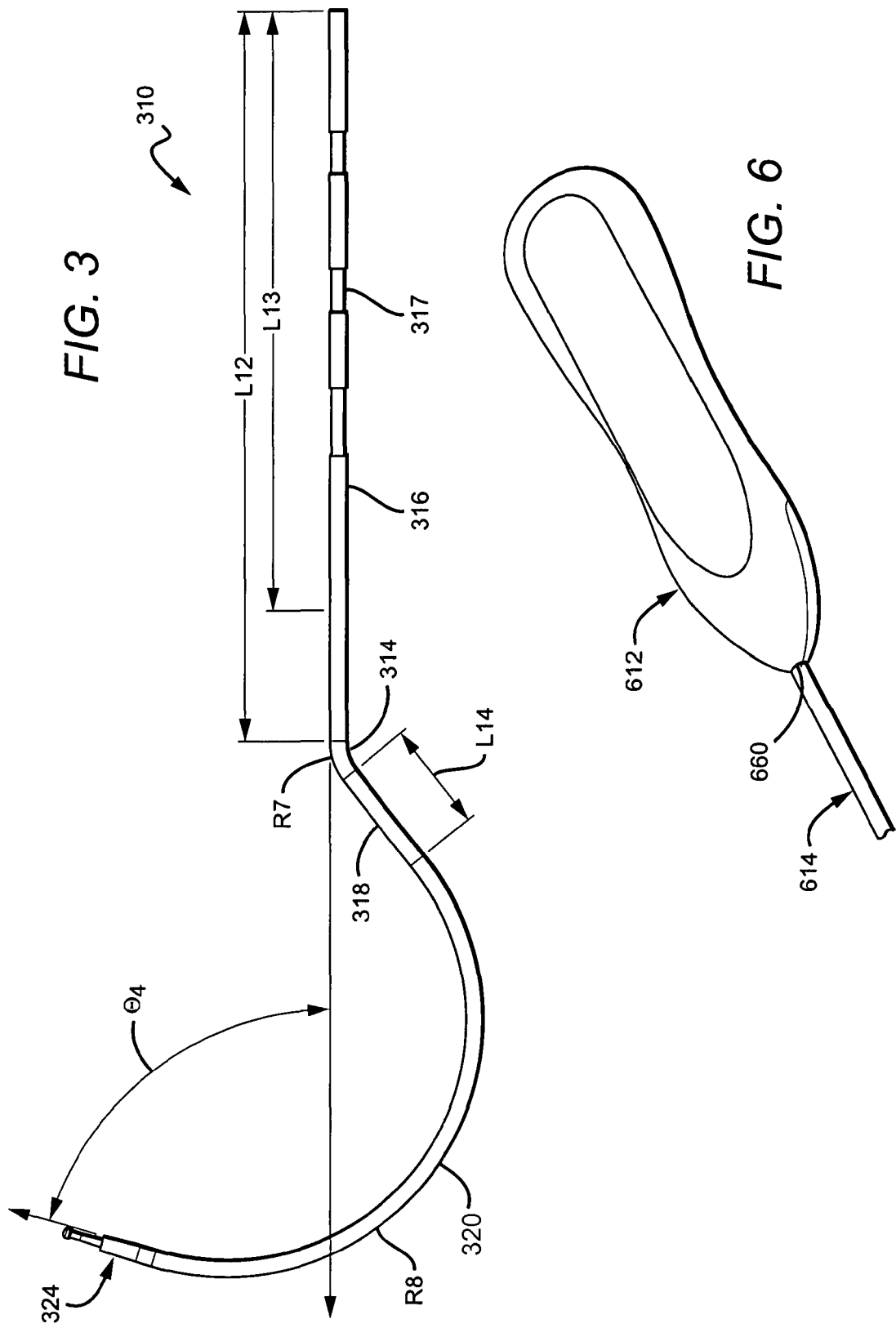

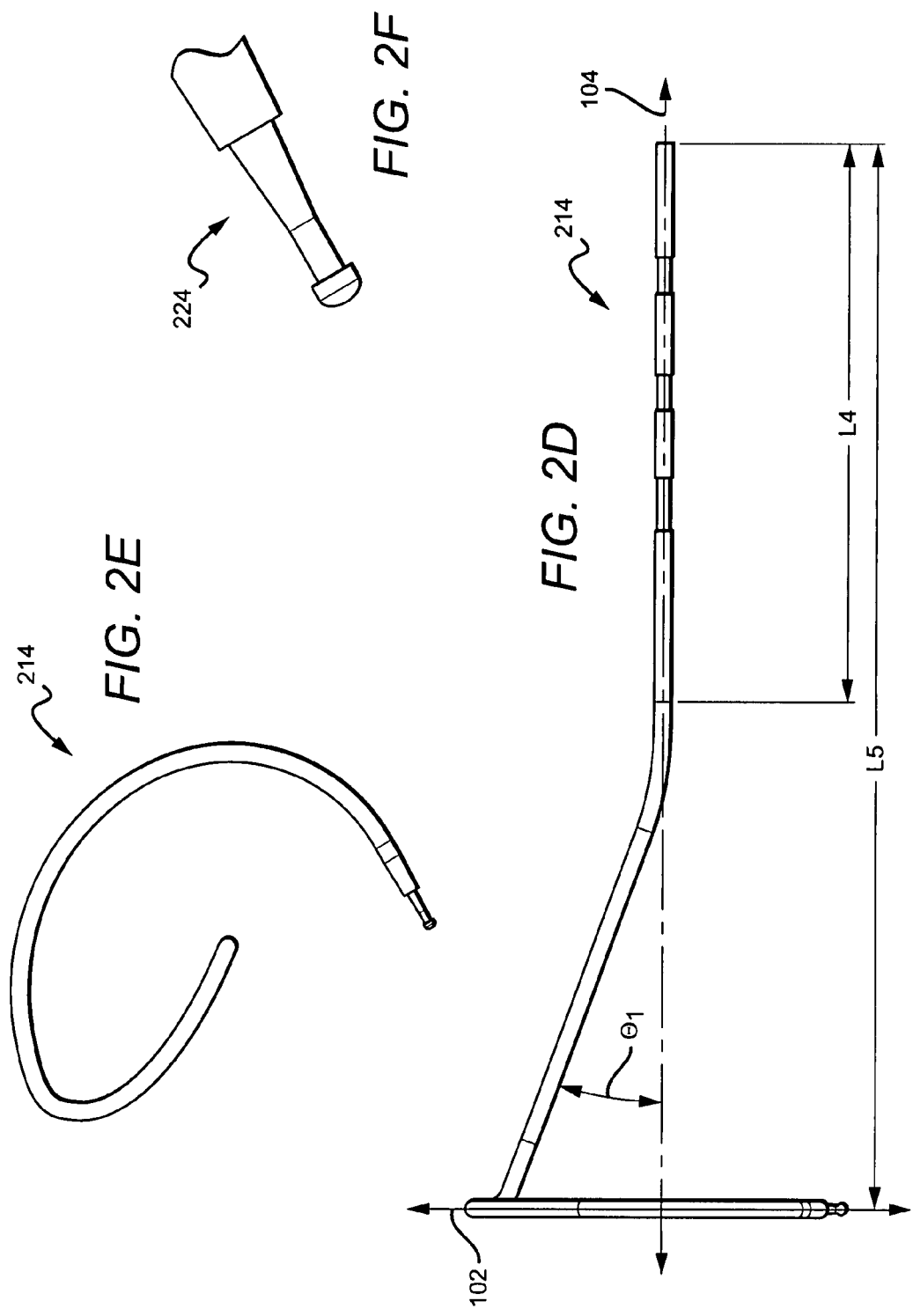

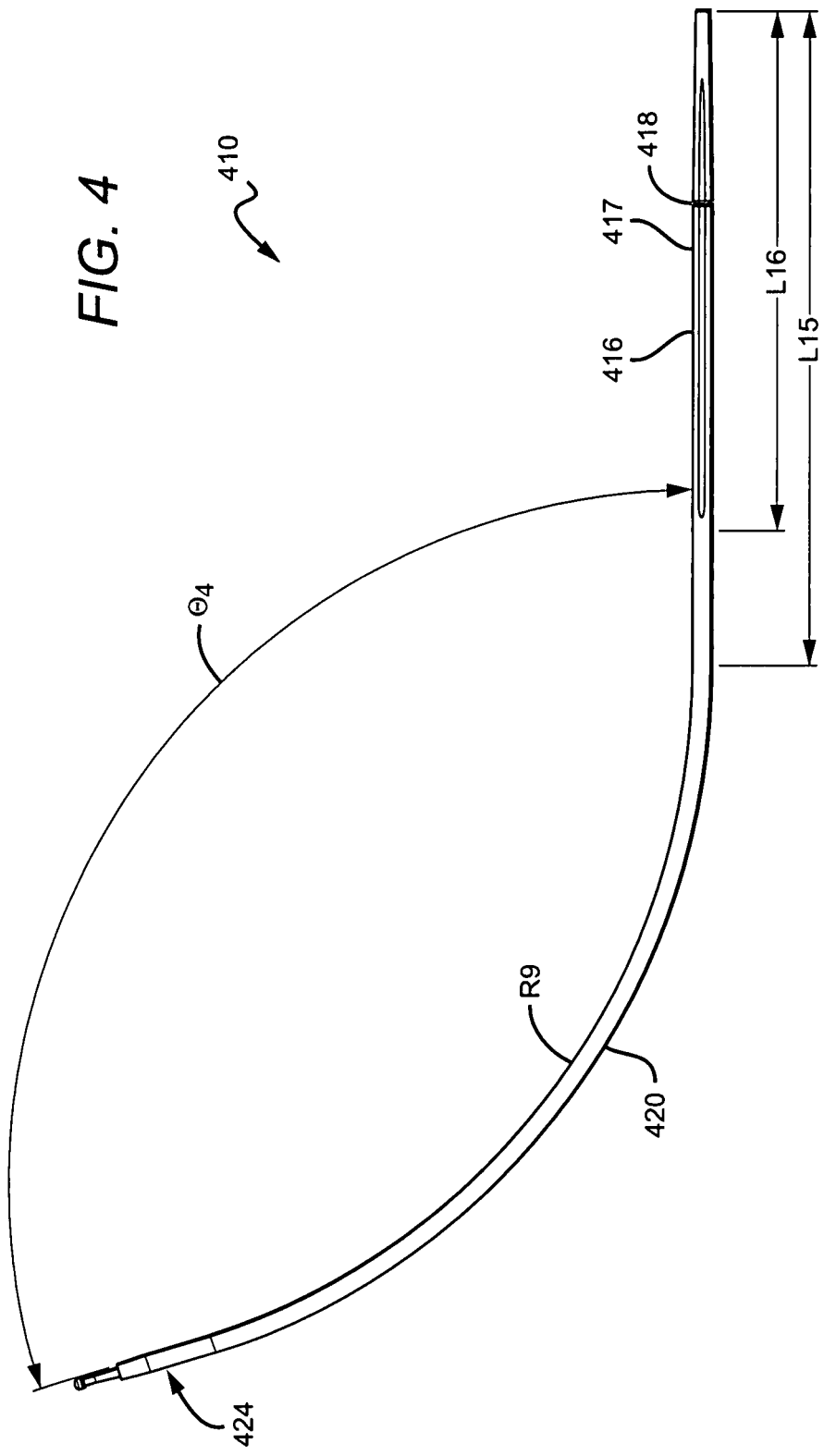

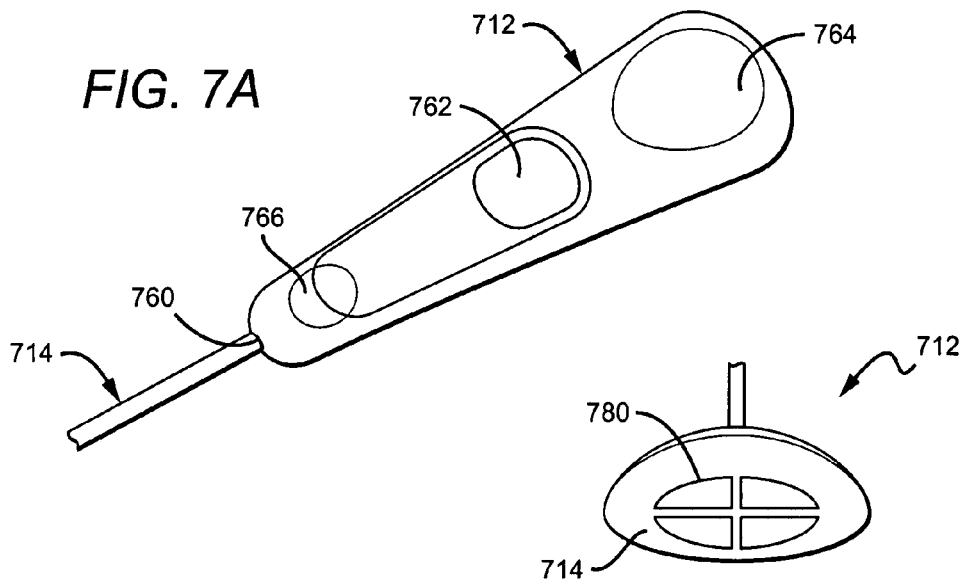
FIG. 7A
FIG. 7B
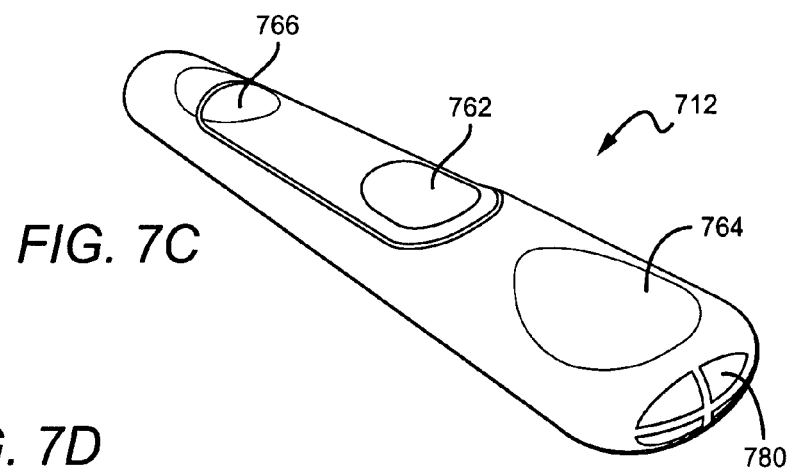
FIG. 7C
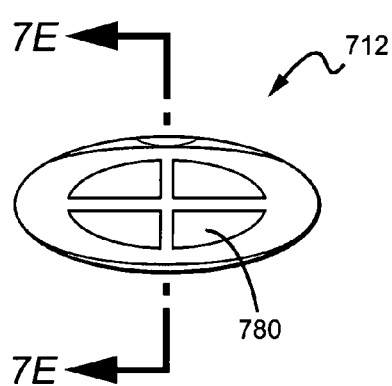
FIG. 7D

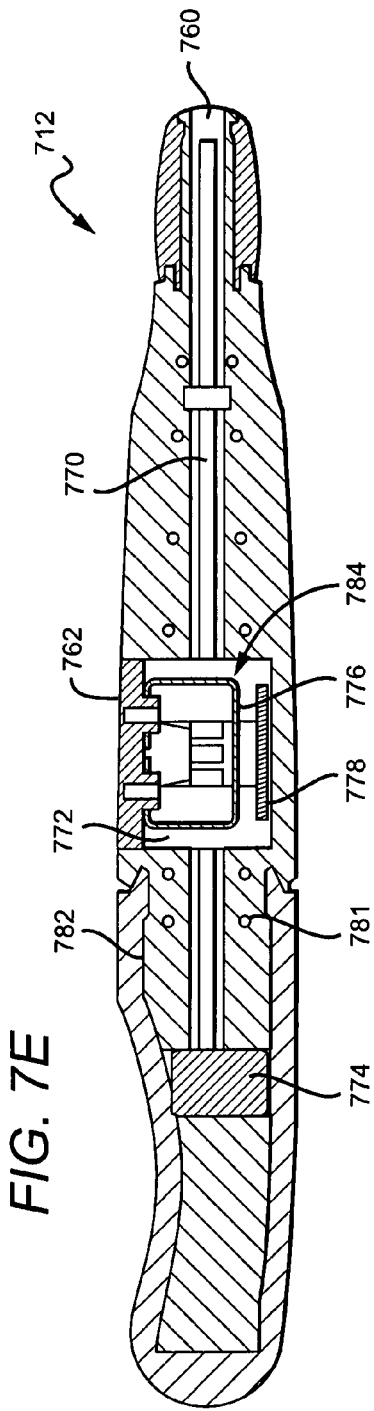

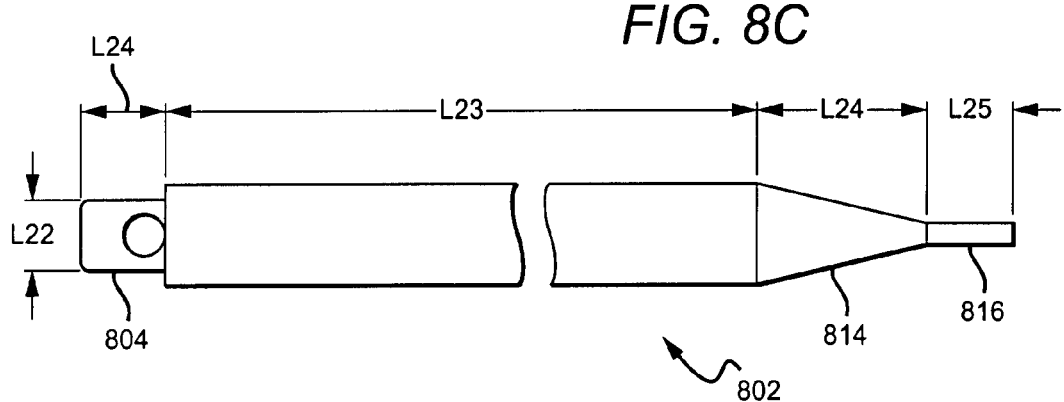
FIG. 8C
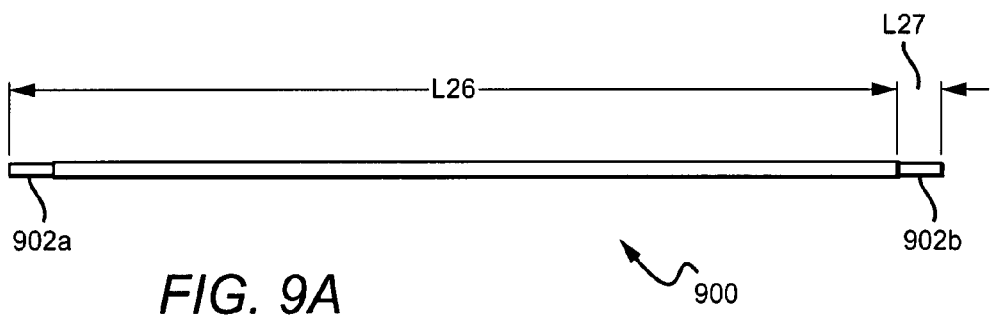
FIG. 9A
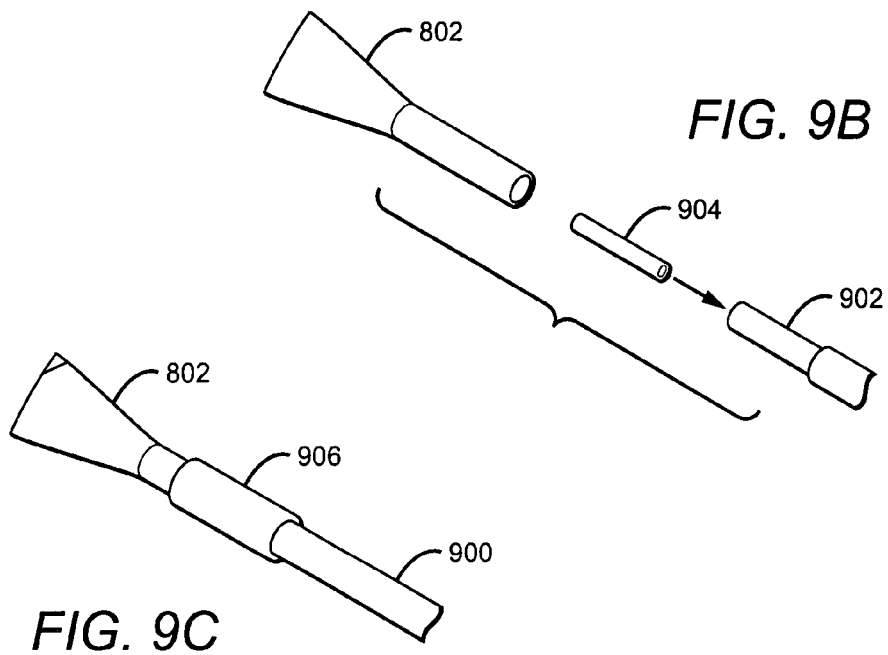
FIG. 9B
FIG. 9C

URETHRAL SUPPORT SYSTEM

PRIORITY

This application is a U.S. national stage application under 35 USC §371 of International Application No. PCT/US2007/078308, filed Sep. 12, 2007, which claims the benefit of priority to U.S. Provisional Patent Application No. No. 60/922,745, filed Apr. 9, 2007, and to U.S. Provisional Patent Application No. No. 60/825,417, filed Sep. 13, 2006, each of which is incorporated by reference into this application as if fully set forth herein.

BACKGROUND

An increasingly widespread technique for treating female urinary incontinence is that of sling suspension. Generally, sling suspension procedures involve the placement of a sling member beneath the patient's urethra. The sling member is preferably implanted in the patient's tissue by using an introducer needle to help draw the tissue implant sling into position. Examples of sling suspension procedures and devices are described, for example, in U.S. Pat. Nos. 5,112,344, 5,899,909, 6,273,852 and U.S. Patent Application Publication No. 2006/0015069, each of which is incorporated by reference in its entirety in this application.

Slings have been made from numerous materials, including both synthetic and natural, and are generally in the form of a mesh. A traditional sling procedure involves placing a strip of an implant material (natural tissue or synthetic mesh) under the urethra and securing it to the rectus fascia or other portions of the patient's anatomy with sutures to hold the implant in position during the healing process.

Recently, however, improved techniques have been developed that speed the implant process by reducing the number of incisions made and altering the pathways by which the tissue implant is introduced into the body. These improvements, which employ specialized instrumentation, help to reduce operative time and have made the procedure less invasive. The improved techniques generally require that an implant be joined to an introducer needle. The implant is then inserted into, and pulled through the body. Subsequently, the implant is detached from the introducer needle. One deficiency with existing introducer devices, however, is that they are typically unwieldy, awkward and time consuming to attach and/or detach to an implant to or from an introducer device.

Applicants have recognized that it would be desirable to provide urethral support systems, including various needle configurations and components, to facilitate the introduction of implants into a body and to provide users with quick and easy identification of components during implantation. Applicants have also recognized that it would be desirable to provide packaging for urethral support systems that would convey to the user exactly what components are enclosed and the type of procedure for which the components are best suited. Thus, described herein are embodiments of urethral support systems and methods of use.

SUMMARY

Accordingly, various embodiments of urethral support systems are described herein. It should be understood that although this disclosure describes the sling suspension of the female urethra, the invention is not to be limited thereto. By way of non-limiting example, it has been determined that the devices and techniques described herein could be modified to support other body organs such as the bowel or bladder. Consequently, all portions of this description should be understood to encompass alternative uses of the embodiments described.

In one embodiment, an introduction device for an implant includes a handle, a first plane bisecting the handle between a top and bottom thereof along a longitudinal axis, and an elongate member having a proximal end including a straight segment coupled to the handle and a distal end terminating in a tip, the elongate member including a first portion defining a first curve and a second portion defining a second curve lying in a second plane perpendicular to the first plane. In another embodiment, an introducer needle includes a proximal section including a feature that enables engagement with a handle, a distal section, and an intermediate section disposed between the proximal and distal sections, the needle including, from a proximal end to a distal end thereof, a straight section, a first curved section, a second curved section having a radius greater than the first curved section, and an introducer tip.

In another embodiment, a kit for introducing an implant includes a first introduction device, including a first handle having a length extending along a longitudinal axis and a first elongate member having a proximal end coupled to a distal end of the handle, the first elongate member including a first curved portion terminating in a tip, the first curved portion lying in a plane perpendicular to the longitudinal axis, a path along the first curved portion from a proximal end to a distal end thereof traveling in a first direction, and a second introduction device, including a second handle having a length extending along a longitudinal axis and a second elongate member having a proximal end coupled to a distal end of the handle, the second elongate member including a second curved portion terminating in a tip, the second curved portion lying in a plane perpendicular to the longitudinal axis, a path along the second curved portion from a proximal end to a distal end traveling in a second direction opposite the first direction.

In one embodiment, a sheath assembly includes a mesh implant, a first section disposed over the first side of the mesh implant, a proximal end of the first section including a first extension forming an angle with respect to a body of the first section in a delivery configuration, a second section separate from the first section disposed over a second side of the mesh implant, a proximal end of the second section including a second extension forming an angle with respect to a body of the second section in the delivery configuration, the first section body and second section body together covering substantially the entire mesh implant in the delivery configuration, and a tab configured for attachment to the first and second extensions.

In another embodiment, a handle for an elongate member includes a core, including a cavity with a first opening in a first side of the core and a channel with a second opening in a distal end of the core, the channel connecting the second opening and the cavity, a skin covering the core, and a locking mechanism configured to at least temporarily secure an elongate member, having a section positioned in the cavity, to the handle.

In still another embodiment, an introduction device for an implant includes an elongate member including a curved portion, and a handle including a body, having a distal end with an opening configured to receive a proximal section of the elongate member and a proximal end including an alignment feature, and a locking mechanism configured to at least temporarily secure the elongate member to the handle.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 1C is a side view of the introducer device of FIG. 1A.

FIG. 1D is a side view of the introducer needle of FIG. 1A without the handle.

FIG. 2A is a perspective view of another embodiment of an introducer device having an introducer needle attached to a handle.

FIG. 2B is a front view of the introducer device of FIG. 2A.

FIG. 2C is a side view of the introducer device of FIG. 2A.

FIG. 2D is a side view of the introducer needle of FIG. 2A without the handle.

FIG. 2E is a partial view of the introducer needle of FIG. 2D.

FIG. 2F is a partial side view of the introducer needle of FIG. 2D showing a distal section and a needle tip.

FIG. 3 is a side view of another embodiment of an introducer needle.

FIG. 4 is a side view of a further embodiment of an introducer needle.

FIG. 6 is a top view of an embodiment of an introducer handle.

FIG. 7A is a top view of another embodiment of an introducer handle.

FIG. 7B is a back view of the introducer handle of FIG. 7A.

FIG. 7C is a perspective view of the introducer handle of FIG. 7A.

FIG. 7D is a further back view of the introducer handle of FIG. 7A.

FIG. 7E is a side cross-sectional view of the introducer handle of FIG. 7D, along the lines 7E-7E.

FIG. 8A is a partial perspective view of a sheath assembly in an unassembled configuration.

FIG. 8B is a partial perspective view of a sheath assembly in an assembled configuration.

FIG. 8C is a top view of a sheath side of a sheath assembly.

FIG. 9A is a top view of a sling tube of a sheath assembly.

FIG. 9B is a perspective exploded view of various components of a sheath assembly connection.

FIG. 9C is a perspective view of FIG. 9B with the sheath assembly components connected.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment. In addition, as used herein, the term "plane" has its ordinary mathematical meaning, including referring to a surface containing all the straight lines that connect any two points on it.

Generally speaking, in accordance with the invention, an implant system involving a needle connector and implant is provided to overcome disadvantages of existing systems. First, it should be understood that although this disclosure speaks of the sling suspension of the female urethra, this invention is not to be limited thereto. By way of non-limiting example, it has been determined that the devices and techniques described herein could be modified to support other body organs such as the bowel or bladder. Consequently, all portions of this description should be understood to encompass such alternative uses of this invention.

Figure 1A:
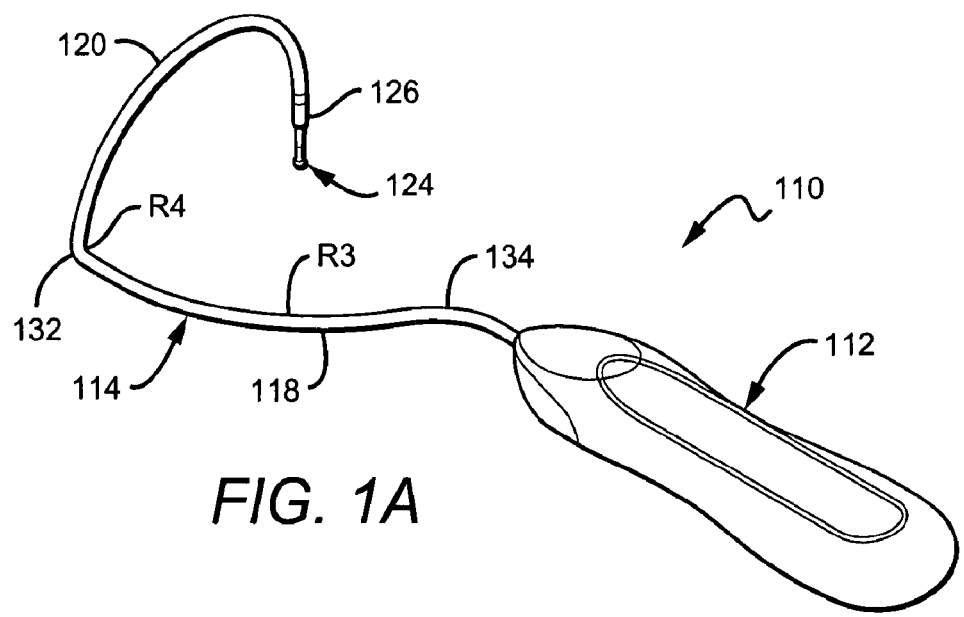
FIG. 1A is a perspective view of an introducer device having an introducer needle attached to a handle.
Figure 1B:
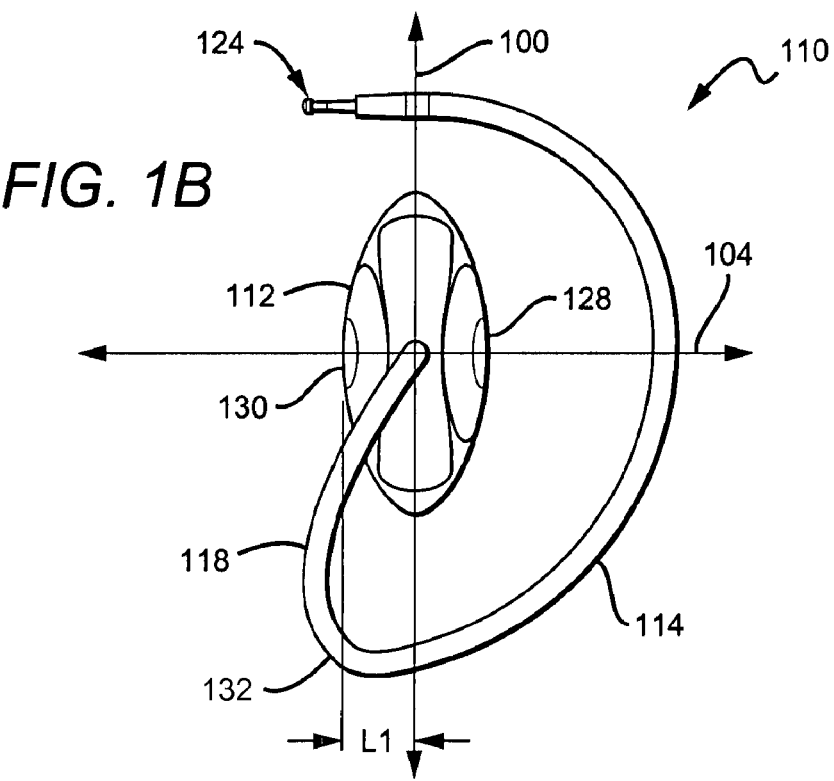
FIG. 1B is a front view of the introducer device of FIG. 1A.

As depicted in FIGS. 1A, 1B and 1C, an introducer device 110 is shown in accordance with various embodiments. As is discussed in further detail below, introducer device 110 may be used to introduce an implant strip, such as, for example, a tissue implant, into a patient. Introducer device 110 includes an introducer handle 112, which is shown attached to an introducer needle 114 with a portion in the shape of a halo. As will be discussed in further detail below, the configuration of the halo needle 114 allows a doctor to insert an implant strip or tissue implant into the patient while navigating around and through various organs and/or other structures within the body of the patient.

The halo needle 114 may be permanently or selectively attached to a handle, but in a preferred embodiment, the halo needle 114 is permanently attached to a handle (e.g., by molding the handle 112 over a proximal end of the needle 114). As shown in FIG. 1D, the halo needle 114 can have a straight segment 116 located at a proximal portion of the halo needle 114. A handle engagement portion 117 of the straight segment 116 can be coupled to the handle 112, as shown in FIGS. 1A, 1B and 1C. Adjacent the straight segment 116 is a first curved portion 118 followed by a second curved portion 120. A needle tip 124 can be located at a distal end 126 of the halo needle 114.

With reference FIG. 1C, the straight segment 116 and handle 112 lie substantially along a first plane 100. The second curved portion 120 lies along a second plane 102, which is substantially perpendicular to the first plane 100. As seen in FIG. 1B, when the halo needle 114 is connected to the handle 112, the first plane 100 bisects the handle along its longitudinal axis. The portion of the handle above the first plane 100 is defined as a top handle portion 128 and the portion below the first plane 100 is defined as a bottom handle portion 130. In addition, the first curved portion 118 lies substantially below the first plane 100 and connects with the second curved portion 120 below the first plane 100 at a distance L1. In one embodiment, the distance L1 is approximately 0.310 inches. As best seen in the bottom view of the halo needle 114 shown in FIG. 1D, the first curved portion 118 can also diverge relative to a third plane 104, which is perpendicular to the first plane 100 and the second plane 102, at an angle $\Theta_1$ of approximately 20 degrees.

Figure 1E:
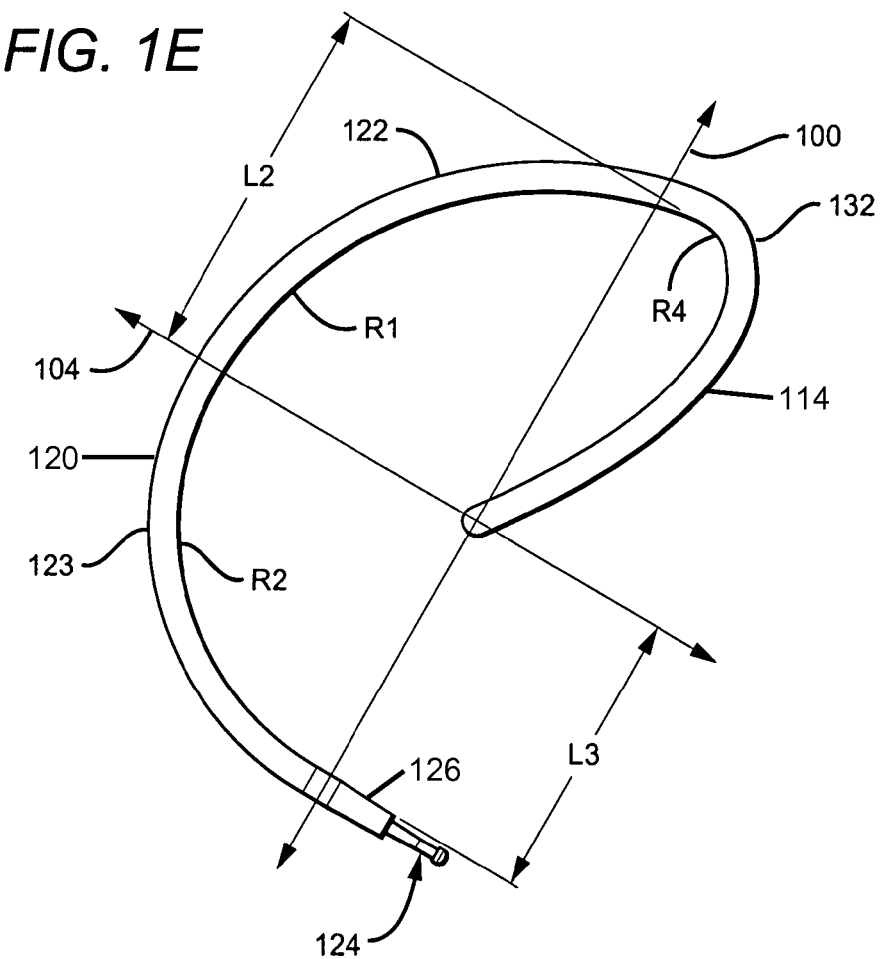
FIG. 1E is a partial view of the introducer needle of FIG. 1D.

The second curved portion 120 can also be asymmetrical with respect to the third plane 104, as best seen in FIG. 1E. The second curved portion 120 can include a first arc 122 extending from a proximal end of the second curved 120 to the third plane 104 and a second arc 123 extending from the third plane 104 to a distal end of the second curved portion 120. In one embodiment, the first arc 122 has a radius of curvature R1 that is greater than a radius of curvature R2 of the second arc 123. For example, in one embodiment, the radius of curvature R1 is approximately 1.44 inches and the radius of curvature R2 is approximately 1.06 inches.

With further reference to FIG. 1E, a first length L2 measured along a straight line in the second plane 102 (second plane 102 is depicted in profile in FIGS. 1C and 1D) from the proximal end of the second curve 120 to the third plane 104 can be greater than a second length L3 measured along a straight line in the second plane 102 from the third plane 104 to the distal end of the second curve 120. In one embodiment, the first length L2 is approximately 1.40 inches and the second length L3 is approximately 1.10 inches. The distal end 126 of the halo needle 114 also can be substantially parallel to the third plane 104, as best seen in FIG. 1B. In addition, as depicted in FIG. 1A, the first curved portion 118 can have a substantially uniform radius of curvature R3. In one embodiment, R3 is about 4.44 inches.

The first curved portion 118 and the second curved portion 120 can be connected at a transition region 132, as best seen in FIGS. 1A and 1E. In one embodiment, the transition region 132 has a radius of curvature R4 of approximately 0.12 inches. Furthermore, the first curved portion 118 can be connected the straight segment 116 at a second transition region 134, as best seen in FIG. 1D. In one embodiment, the second transition region 132 has a radius of curvature R5 of approximately 1.00 inch.

In general, it has been found that the shape of the halo needle 114 provides several benefits. For example, the curvature of the halo needle 114 has been found to provide easier passage while navigating around and through various organs and/or other structures within the body of the patient. The curvature of the halo needle 114 has also been found to allow easier rotation and exteriorization of the needle tip 124. In addition, the curvature of the halo needle 114 can provide an axis of rotation at a mid-point of the device 110, which can advantageously mimic a helical rotation.

Other dimensions of the introducer needle 120 have also been found to be beneficial in accordance with one embodiment. With reference to FIG. 1D, the straight segment has a length L4 measured along a straight line in the first plane from its proximal end to its distal end of about 3.75 inches and the halo needle 114 has a length L5 measured along a straight line in the first plane from the introduction needle's proximal end to the second plane 102 in the range of about 7.25 inches to about 7.50 inches, preferably approximately 7.37 inches. Referring to FIG. 1C, when the handle 112 is attached to the halo needle 114, a length L6 measured along a straight line in the first plane 100 from a proximal end of the handle 112 to the second plane 102 is in the range of about 8 inches to about 9 inches, preferably approximately 8.76 inches. In addition, a length L7 measured along a straight line of the first plane from a distal end of the handle 112 to the second plane 102 is in the range of about 3 inches to 4 inches, preferably approximately 3.87 inches.

Figure 1F:
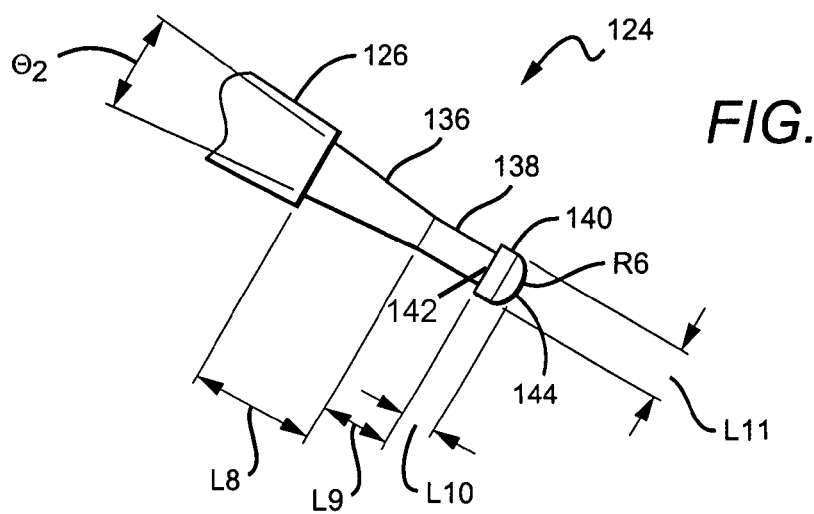
FIG. 1F is a partial side view of the introducer needle of FIG. 1D showing a distal section and a needle tip.

FIG. 1F illustrates the introducer needle distal end 126 and the needle tip 124. The tip 124 has a tapered portion 136 with a frusto-conical shape connected to a shaft portion 138 with a cylindrical shape. The shaft portion 138 is connected to a barb 140. The barb 140 has a generally flat part 142 and a front part 144 having semi-spherical shape. The shape of the needle tip 124 has been found to have several benefits, including providing easier insertion and passage, having a smaller profile, and being less sharp than other devices. Certain dimensions for the configuration of the tip 124 have been found to be beneficial in accordance with one embodiment. With reference to FIG. 1F, the tapered portion 136 is tapered at an angle $\Theta_2$ of about 11 degrees and has a length L8 of about 0.164 inches. The shaft portion 138 has a longitudinal length L9 of about 0.090 inches. The barb 140 has longitudinal length L10 of about 0.060 inches and a maximum thickness L11 in the range of about 0.068 inches to about 0.072 inches, preferably approximately 0.070 inches. The front part 144 of the barb has a radius of curvature R6 in the range of about 0.030 inches to about 0.040 inches, preferably approximately 0.035 inches.

FIGS. 2A-2C show an introducer device 210 including an introducer needle 214 with a portion in the shape of a halo attached to a handle 212. FIGS. 2D and 2E show the halo needle 214 without an introducer handle. FIG. 2F shows a distal portion of the halo needle 214 and a needle tip 224. In one embodiment, the introducer device 210 has the same shapes and dimensions as the introducer device 110 shown in FIGS. 1A-1F and discussed above, but the halo needle 214 curves in the opposite direction as the halo needle 114. For example, if introducer devices 110 and 210 were placed side-by-side (with handles adjacent to one another), either the proximal end of the second curved portion of halo needle 214 would be adjacent the proximal end of the second curved portion of halo needle 114 or the distal end of the second curved portion of halo needle 214 would be adjacent the distal end of the second curved portion of halo needle 114. As will be explained in more detail below, the introducer device 110 and the introducer device 210 can be beneficially used in the same procedure. For example, the introducer device 110 can be used on one side of a patient and the introducer device 210 can be used on the other side of the patient. By doing so, the procedure can be performed in a more beneficial manner. As with the halo needle 114, the halo needle 214 may be permanently or selectively attached to a handle, but in a preferred embodiment, the halo needle 214 is permanently attached to a handle (e.g., by molding the handle 112 over a proximal end of the needle 214).

With reference to FIG. 3, there is shown another embodiment of an introducer needle, hook needle 310. The hook needle 310 can be used to perform various surgical procedures, including a transobturator implant deliver procedures. The hook needle 310 can include a first straight segment 316 at its proximal end, a second straight segment 318 connected to the first straight segment 316 via a transition area 314, and a curved portion 320. A tip 324 is then connected to curved portion 320 at a distal end of the hook needle 310. The first straight segment 316 can also include a handle engagement portion 317 configured to attached to a handle, such as one of the handles described herein. As shown in FIG. 3, the hook needle 310 can lie along a single plane (not shown). Preferably, the hook needle 310 is permanently attached to a handle, such as handle 612, through a molding process.

Certain dimensions for the configuration of the hook needle 310 have been found to be beneficial in accordance with one embodiment. The straight segment 316 can have a longitudinal length L12 of about 4.25 inches and the handle engagement portion 317 can have a longitudinal length L13 of about 3.50 inches. The transition region 334 can have a radius R7 of about 0.25 inches. The second straight segment 318 can have a length L14 of about 0.64 inches. The curved portion 320 can have a radius R8 of about 1.41 inches. The tip 324 can have the same dimensions as the tip 124 described above with reference to FIG. 1F. An angle $\Theta_3$ of the tip 324 relative to the first straight segment 316 can be about 75 degrees.

With reference to FIG. 4, there is shown another embodiment of a needle 410 for an introducer device including a handle (e.g., handle 712 in FIG. 7A). The needle 410 can be used in various surgical procedures, including a suprapubic implant delivery procedure. The needle 410 can include a straight segment 416 at its proximal end. A curved portion 420 can be connected at a distal end of the straight segment 416. A tip 424 can be connected to a distal end of the curved portion 420. The tip 424 can be similar or the same as the tip 24 described with reference to FIG. 1F. The straight segment 416 can also include a handle engagement portion 417 configured to be attached to a handle, such as one of the handles disclosed herein. As shown in FIG. 4, the needle 410 can lie along a single plane. Certain dimensions for the configuration of the needle 410 have been found to be beneficial in accordance with one embodiment. The straight segment 416 can have a length L15 in the range of about 4.36 inches to about 4.48, preferably approximately 4.42 inches and the handle engagement portion 317 can have a length L16 in the range of about 3.25 inches to about 3.75 inches, preferably approximately 3.50 inches. The curved portion 320 can have a radius R9 of about 4.75 inches. The tip 424 can have the same dimensions as the tip 124 described above with reference to FIG. 1F. An angle $\Theta_4$ of the tip 424 relative to the first straight segment 416 can be about 108 degrees.

Figure 5:
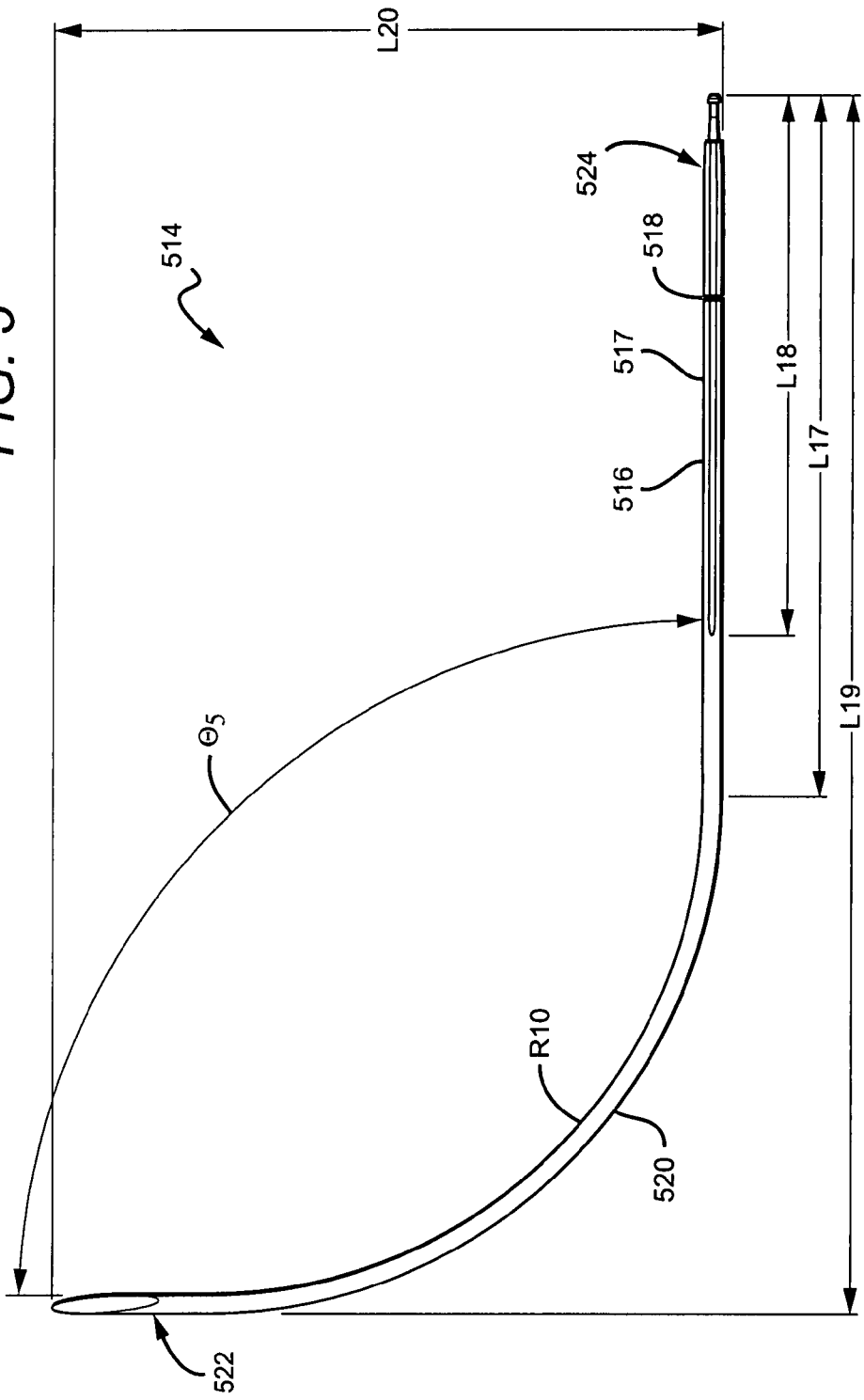
FIG. 5 is a side view of yet another embodiment of an introducer needle.

With reference to FIG. 5, there is shown yet another embodiment of a needle 514 for use with a introducer device including a handle (e.g., handle 712 in FIG. 7A). The needle 514 can be used in various surgical procedures, including a retropubic implant delivery procedure. A needle tip 524 is located at a proximal end of the needle 514. Connected to the needle tip 524, is a straight segment 516 followed by a curved segment 520. A beveled tip 522 is located at a distal end of the needle 514. In one embodiment, the beveled tip 522 is inserted through a patient, where the bevel assists in dissecting through the tissue. Once passed, a handle, such as one of the handles described herein, can be removed from a proximal end of the needle 514, and the tip 524 can then be attached to a tissue implant. Exemplary surgical techniques using the needle 514 are described in more detail further below. Certain dimensions for the configuration of the needle 514 have been found to be beneficial in accordance with one embodiment. The straight segment 516 can have a length L17 in the range of about 4.36 inches to 4.48 inches, preferably approximately 4.42 inches and the handle engagement portion 517 can have a length L18 in the range of about 3.25 inches to about 3.75 inches, preferably approximately 3.50 inches. The curved portion 520 can have a radius R10 of about 3.1 inches. The angle $\Theta_5$ of the beveled tip 522 relative to the straight segment 516 can be about 90 degrees. The beveled tip 522 can have a length of about 1 inch. The tip 524 can have the same dimensions as the tip 124 described above with reference to FIG. 1F. The needle 514 can lie along a single plane, where the length L19 measured in a straight line from the tip 524 to the tip 522 can be in the range of about 7.50 inches to about 8.00 inches, preferably approximately 7.69 inches and the length L20 can be in the range of about 4.15 inches to about 4.50 inches, preferably approximately 4.27 inches.

A top view of one embodiment of an introducer handle 612 attached to an introducer needle 614 is shown in FIG. 6. The introducer handle 612 can have an opening 660 at its distal end to attach to the proximal end of the introducer needle 614. An operator of an introducer device can grasp the handle 612 for performing a procedure. The exterior of the handle can also have textured elastomer material for providing an improved grip and appearance. In one embodiment, the handle 612 is similar to, or the same as, handle 112 described above, and may be used with halo needles or hook needles during trans-obturator procedures.

FIGS. 7A-7B show another embodiment of an introducer handle 712 attached to an introducer needle 714. Handle 712 can be used in various surgical procedures, for example during a retropubic or suprapubic procedure. In addition, the introducer handle 714 can be selectively attached to, and detached from one or more of the introducer needles described herein, as well as with other introducer needles known in the art. With further reference to FIG. 7A, the introducer handle 712 can have an opening 760 at its distal end to attach to the proximal end of the introducer needle 714. The handle 712 also has a pushbutton 762 located on one side of the handle 612. Gripping depressions 764 and 766 can be formed in the handle 712 for providing for better gripping of the handle 712 during a surgical procedure.

FIG. 7B shows an artificial horizon 780 feature formed on a back side of the handle 712 in accordance with one embodiment. As used herein, the term "artificial horizon" can refer to a visual indicator that aids a user in navigating the device through a patient, for example. In other words, an artificial horizon can provide a user with visual directional aid during a needle passage. In the embodiment shown in FIG. 7B, the artificial horizon 780 includes a cross-hair pattern formed on a back side of the handle 714. By viewing the position of the artificial horizon 780 relative to another object, a user can determine, for example, the rotation of a needle attached to the handle 712 relative to the other object.

FIG. 7C shows a side perspective view of the handle 712, FIG. 7D shows a back view of the handle 712, and FIG. 7E is a side cross-sectional view of the handle 716 along the line 7E-7E shown in FIG. 7D. With reference to FIG. 7D, the handle 712 includes a core 781 with an interior portion defining a cavity 772 and an axial channel 770. The axial channel 770 extends from the opening 760 in the distal end of the handle, through a proximal side of the cavity 772, out a distal side of the cavity 772, and ending at a stop pin 774. A skin material 782 can cover all or just a portion of the core 781. The skin material 782 can be a textured elastomeric material for providing improved gripping and appearance. In addition, a locking mechanism 784 is positioned in the cavity 772. The locking mechanism 784 is configured to at least temporarily secure a proximal end of an elongate member, such as an introducer needle, to the handle 712. In the embodiment shown in FIG. 7E, the locking mechanism 784 includes a retainer 776, a spring 778 positioned under the retainer 776, and a pushbutton 762 positioned in a top opening of the cavity 772 and connected to the retainer 776.

The retainer 776 is positioned between the spring 778 and pushbutton 762 and in one embodiment is shaped like a bracket, including an opening in a side adjacent the proximal side of the cavity 772. The opening may be shaped like an inverted teardrop with the large portion of the teardrop shape adjacent the pushbutton (or top of the cavity 772) and the small portion of the teardrop shape adjacent the spring (or bottom of the cavity 772). The pushbutton 762 is biased in a closed position by the spring 778, such that to insert a needle portion into (or through) the chamber requires depression of the pushbutton 762, which in turn moves the retainer 776 so that the large portion of the teardrop shape (or other shaped opening of the retainer) is in-line with the channel 770 and passage of a needle into or through the chamber is permitted. Release of the pushbutton 762 causes the spring 778 to move the retainer 776 upward so that the small portion of the teardrop shape is coincident with the channel 770. Thus, a needle portion inserted into or through the cavity 772 will be tightly gripped by the retainer 776, preventing axial movement thereof.

To further enhance the engagement between the retainer and the needle inserted into or through the cavity 772, the needle may be configured with a notch or other engagement feature, such as the circumferential notches 418 and 518 on needles 410 and 510, respectively (FIGS. 4 and 5). With respect to the needles 410 and 510, the notches 418 and 518 may be spaced a distance from the proximal end of the needle such that when the proximal end is inserted through the cavity 772 and into contact with the stop pin 774, the notches 418 and 518 are aligned with a side wall of the retainer (on either side of the cavity 772). Moreover, the notches may have a thickness at least slightly greater than the thickness of the retainer side wall such that the portion of the side wall engaging the needle (e.g., the inner edge of the opening) is received within the notch.

In accordance with one embodiment, an introducer needle, such one of the introducer needles described above, can be selectively attached and detached from the handle 712. To attach an introducer needle to the handle 712, a proximal end of the introducer needle is inserted into the opening 760 and pushed through the axial channel 760 and the retaining chamber 772 until the proximal end hits the stop pin 774. The introducer needle can be selectively detached from the handle 712 by pressing the button 762 and pulling the needle proximal end out of the axial channel 760. It is understood that other types of locking mechanisms known in the art can also be used.

Various features of a sheath assembly 800 are described with reference to FIGS. 8-9. The sheath assembly 800, in one embodiment, includes two sheath sides, two sling tubes, a sheath tab and two connectors, each of which are described in more detail below. FIG. 8A is a partial view of a first sheath side 802a and a second sheath side 802b, both of which make up a portion of the sheath assembly 800. In one embodiment, the first sheath side 802a is very similar or identical to the second sheath side 802b. The sheath sides are preferably made of a material with a low coefficient of friction, such as polytetrafluoroethylene (PTFE). A first side of a mesh implant (not shown) can be disposed inside the first sheath side 802a and a second side of the mesh implant (not shown) can be disposed inside the second sheath side 802b. A proximal end of the first sheath side 802a has a first extension 804a forming an angle $\Theta_6$ with respect to a body of the first sheath side. Similarly, a proximal end of the second sheath side 802b has a second extension forming an angle $\Theta_7$ with respect to a body of the second sheath side when placed in a delivery configuration. As manufactured, the extensions 804a, 804b may be parallel extensions of their respective sheath sides, such that they need to be manually bent or configured into angles $\Theta_6$, $\Theta_7$. Alternatively, the extensions 804a, 804b may be manufactured with pre-fashioned angles $\Theta_6$, $\Theta_7$. In one embodiment, angles $\Theta_6$ and $\Theta_7$ are each approximately 90 degrees.

The sheath assembly is shown in a delivery configuration in FIG. 8B, in which a tab 806 is attached to the first and second extensions 802a and 802b. In one embodiment, the tab 806 includes a slot 808 configured to permit sliding of the first and second extensions 802a and 802b therethrough, as shown in FIG. 8A. The tab 806 may include an adhesive on at least a portion of an inner surface thereof to facilitate adhesion of the tab 806 to the extensions 802a and 802b or to itself. The tab 806 can also be heat-sealed over the extensions 802a and 802b. In one embodiment, the tab 806 is made of Tyvek®, which is commercially available from DuPont, Inc. In addition, the tab 806 can have a visual indicator. As seen in FIGS. 8A and 8B, the visual indicator can be arrows 810a and 810b on opposing sides of the tab 806. In one embodiment, the tab 806 has a color to match the color of the sheath assembly, handle, or other features of the introducer kit. In one embodiment, a portion 812 of the tab 806 can be offset for providing easy gripping of the tab 806 and peeling apart the tab 806. FIG. 8C shows the sheath side 802 with the extension 804 in the manufactured straight configuration (as opposed to the angled configuration shown in FIGS. 8A and 8B).

Certain dimensions of the sheath side 802 have been found to be beneficial in accordance with one embodiment. With reference to FIG. 8C, a length L21 of the second extension can be about 0.50 inches and the width L22 of the second extension can be about 0.4 inches. The length L23 of the sheath side can be about 10.0 inches and the length L24 of the tapered section can be about 1.0 inch. The length L25 of the coupling section can be about 0.50 inches.

With reference to FIG. 9A, a distal section of the sheath side 802 can include a tapered section 814 connected to a coupling section 816 for attachment to a sling tube 900. In one embodiment, distal and proximal ends of the sling tube 900 can have respective reduced diameter sections 902a and 902b, each reduced diameter section 902a and 902b configured to be inserted into one of the coupling section 816 and a needle connector, for example. In another embodiment, only one end (e.g., 902a) of the sling tube 900 has a reduced diameter section for insertion into coupling section 816, while the other end (e.g., 902b) has the same diameter as the body of the sling tube 900 for receipt of a connector end, such as connector stem 1006, discussed in more detail below. In one embodiment, the sling tube 900 has a length L26 of about 8.0 inches (8 to 9 inches preferably), and the reduced diameter section 902 has a length L27 of about 0.75 inches.

FIGS. 9B and 9C illustrate a connection between the sheath side 802 and the sling tube 900 in accordance with one embodiment. A rod 904 (e.g., made of stainless steel) can be inserted into one of the reduced diameter sections 902. The reduced diameter section 902 can then be inserted into the coupling section 816 of the sheath side 802. With reference to FIG. 9D, a crimp 906 can be swaged around the area between the coupling section 816 and the sling tube 900. In one embodiment, prior to assembling this section of the sheath assembly 800, a primer is applied to the inner diameter of the coupling section and adhesive is applied to the outer diameter of the reduced diameter section for providing a secure connection. The sling tube 900 may be of a different color than the sheath to provide a clear indication to the surgeon during cytoscopy where the sheath side 802 ends and the sling tube 900 begins. In one embodiment, the sling tubes 900 of a sheath assembly 800 are similar in color to other features of the sling assembly and/or packaging for the introducer kit as described herein. For example, in one embodiment, the sling tubes 900 have a green color, along with the sheath tab 806, and the packaging for the introducer device used therewith (e.g., the introducer device 110 and 210), while the sheath sides (e.g., made of PTFE) are clear (e.g., transparent) so that the mesh implant can be seen.

As described above, a tissue implant or support strip can be secured to an introducer needle for introducing the tissue strip of support strip into a patient, for example. In accordance with various embodiments, a connector may be used to facilitate connection between a tissue implant and an introducer needle. Advantageously, a connector can provide selective attachment and detachment of implants to and from an introducer needle.

Figure 10A:
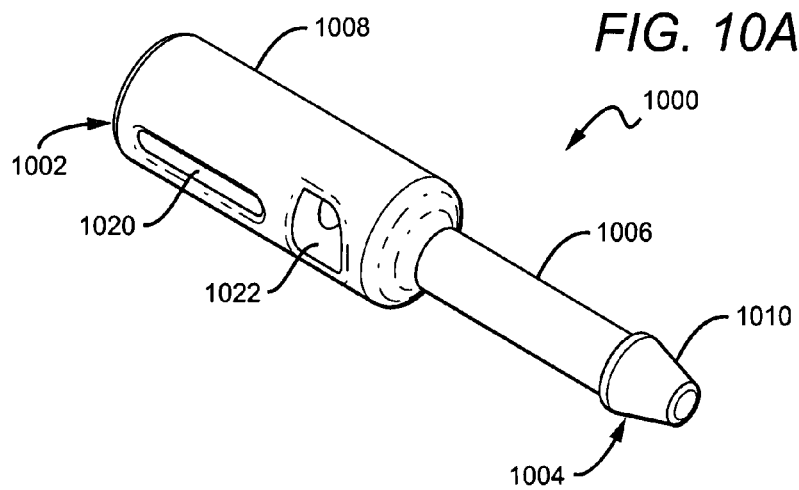
FIG. 10A is a perspective view of a sheath assembly connector.
Figure 10B:
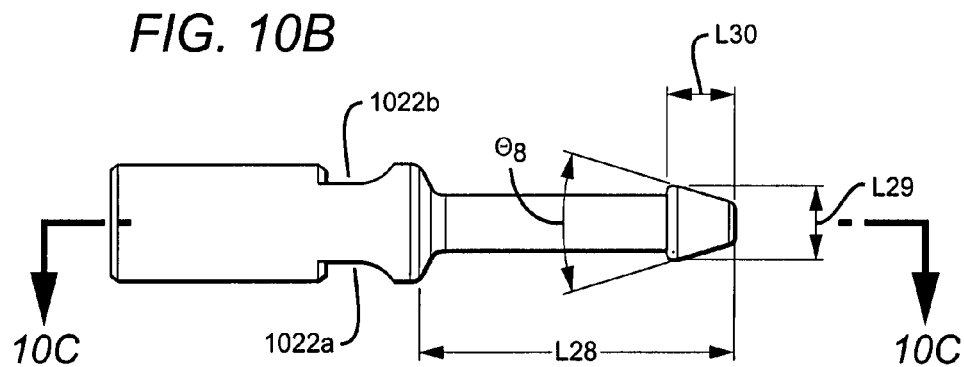
FIG. 10B is a top view of the sheath assembly connector of FIG. 10A.
Figure 10C:
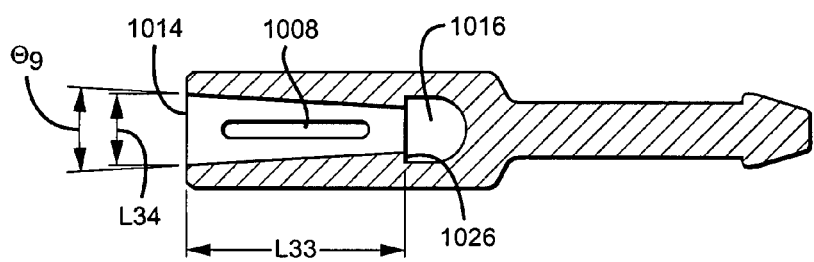
FIG. 10C is a cross-sectional view of the sheath assembly connector of FIG. 10B, across the line 10C-10C.

With reference to FIGS. 10A-10C, there is shown an embodiment of a sheath assembly connector 1000. Connector 1000 has a proximal end 1002 and a distal end 1004. Proximal end 1002 is designed for connecting to an introducer needle, such as the introducer needles described herein, and the distal end 1004 includes a stem 1006 designed for insertion into a receiving member. For example, the distal end 1004 can be inserted into the end of the sling tube 900 opposite the end attached to the sheath side 802. The stem 1006 projects from a main body 1008 and a barb 1010 is located at the distal end of the stem 1006. The barb 1010 and all or a portion of the stem 1006 can be inserted into a corresponding opening of a sheath or other member coupled to the tissue implant. For example, the distal end 1004 of the connector 1000 can be inserted into an end of the tube 900 and a crimp swaged over the tube and distal end to secure the connector 1000 to the tube 900.

With reference FIG. 10C, the main body 1008 includes a cavity 1012. The cavity 1012 can be sized and shaped to be approximately equivalent to the size and shape of a needle tip. Accordingly, an opening 1014 can be located on one side of the cavity 1012 and a semi-spherical shaped portion 1016 located on the other side, a tapered lumen section 1018 located between the opening 1014 and the semi-spherical shaped portion 1016. The semi-spherical shaped portion 1016 can be approximately equivalent to the shape of a needle tip. With reference to FIG. 10A, the connector 1000 can also have various cutout sections. For example, side cutouts 1020 and 1022 can be provided, with respective identical cutouts located on the opposite side of the connector 1000. The cutouts 1010 and 1022 can be designed to provide detectable feedback to a user. For example, the connector 1000 can provide one or more clicking noises to notify a user that the needle has been properly inserted into the connector 1000.

The tissue connector 1000 may be quickly and easily attached or coupled to an introducer needle by inserting a needle tip of an introducer needle into the cavity 1008 of the tissue connector 1000. The tissue connector 1000 can also be quickly and easily removed from the introducer needle by pulling the connector 1000 off of and away from the end of the introducer needle such that the needle is removed from the cavity 1008 of the connector. A benefit of such a design, whereby the tissue connector 1000 may be easily and quickly attached to an introducer needle or removed therefrom, is that it facilitates easy placement of the tissue implant to the needle and thus speeds up the implanting procedure as will be described in further detail below. The connector 1000 may be made of a polypropylene material to facilitate removal of the needle. Alternatively, or following removal of the needle, the tube (or other component attached to the needle) may be severed proximal of the connector attachment point to permit the surgeon to insert the needle tip into the tube for an additional pass through the tissue. In a preferred embodiment, the tube is configured with dimensions to provide a friction fit with the needle tip for such a procedure.

In one embodiment, the tissue connector 1000 has a profile (e.g. outside diameter) such that a generally constant diameter is provided from the connector 1000 to a member to which it is attached, such as the sling tube 900. Such a profile can reduce drag when pulling the needle and tube through a patient's tissue.

Certain dimensions for the configuration of the tissue connector 1000 have been found to be beneficial in accordance with various embodiments. With reference to FIG. 10B, the length L28 of the stem 1006 and barb 1010 can be about 0.350 inches. The barb 1010 can have a large diameter L29 of about 0.017 inches, and a length L30 of about 0.076 inches. A tapered portion 1024 of the barb 1010 has an angle $\Theta_8$ in the range of about 28 degrees to about 32 degrees, preferably about 30 degrees. With reference to FIG. 10C, the total length L31 of the connector 1000 can be in the range of about 0.67 inches to about 0.71 inches, preferably about 0.69 inches, and the main body 1008 can have a length L32 of about 0.34 inches. The tapered lumen section 1018 can have a length L33 of about 0.24 inches and be tapered at an angle $\Theta_9$ of about 7.5 degrees. A neck area 1026 located where the lumen section 1018 and the semi-spherical portion 1016 connect can have an interior diameter L34 of about 0.050 inches.

Figure 11A:
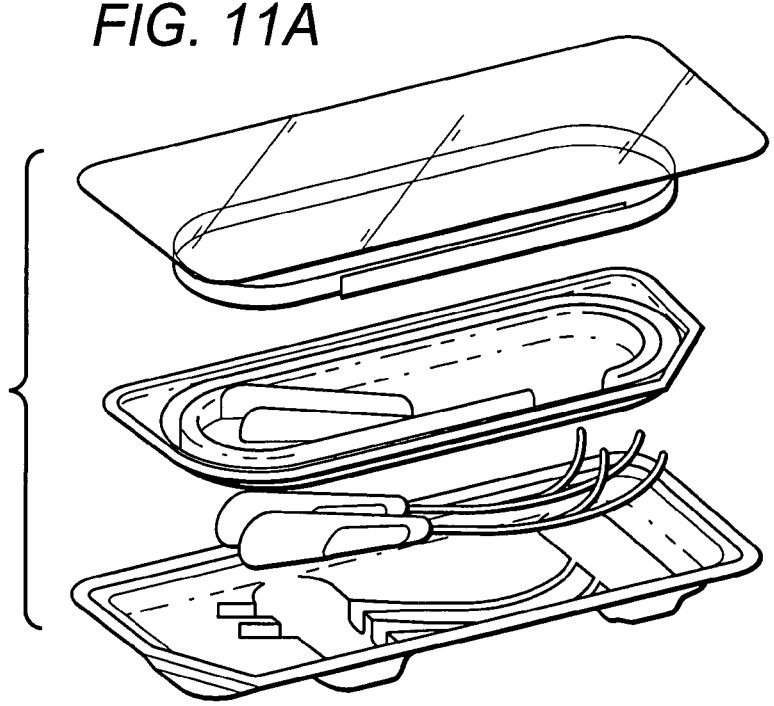
FIG. 11A is an exploded view of one embodiment of an internal packaging configuration.
Figure 11B:
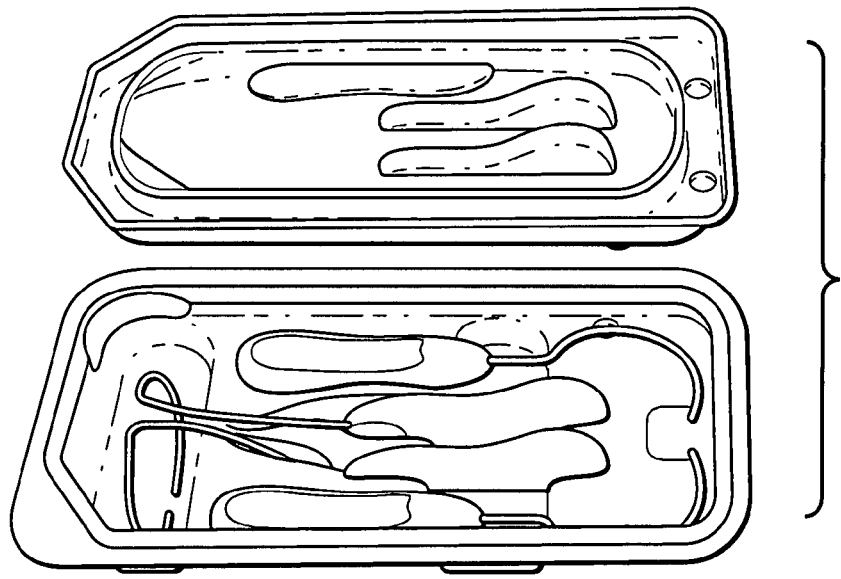
FIG. 11B is an exploded view of another embodiment of an internal packaging configuration.

In one embodiment, various needles, handles, and sheath assembly components are included in a kit for placing a sling suspension in a body, for example under a female urethra. The kit may be packaged in a box including introducer devices for a particular procedure (as described below), as well as a sheath assembly including a mesh implant, as described herein. The packaging may include internal packaging with a single tray design, such as shown in FIGS. 11A and 11B, including a retainer tray used to house the sheath assembly and hold the needles in place (FIG. 11A). FIG. 11A shows one side of the tray design, while FIG. 11B shows the opposite side (i.e., upside down from FIG. 11A). Certain needles described herein are shown combined together in the trays of FIGS. 11A and 11B, although this is for illustrative purposes and shows only two potential packaging embodiments for an introducer system as contemplated herein.

Figure 12A:
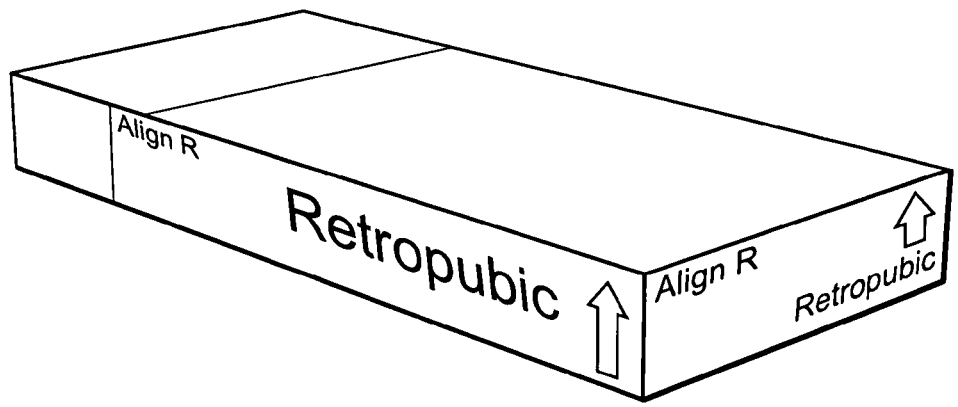
FIG. 12A is an illustration of one embodiment of an outer packaging configuration.
Figure 12B:
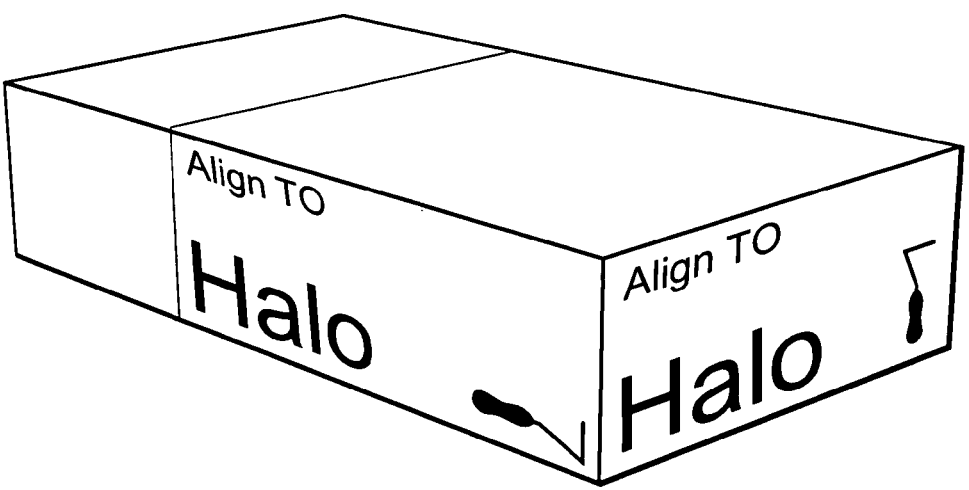
FIG. 12B is an illustration of another embodiment of an outer packaging configuration

FIGS. 12A and 12B illustrate further embodiments of packaging for the introducer system described herein, showing a box in which the trays are housed. Notable on the boxes or outer packaging is the use of easily identifiable watermarks that quickly impart to the user which needle introduction system is held therein, as well as descriptors (e.g., letters or symbols) to indicate the procedure for which the product is suitable. For example, with respect to letter descriptors indicating the type of procedure for the introducer system in the package, the letter "R" could represent a retropubic system, the letter "S" could represent a suprapubic system, the letters "RS" could represent both retropubic and suprapubic systems, and the letters "TO" could represent a trans-obturator system (e.g., hook needle 310, halo needles 114 and 214, or a combination thereof). Also notable is the use of a particular color on the outer packaging (e.g., green) to match other features of the introduction system (e.g., sling tubes, sheath tab, etc.) for branding purposes, the use of silhouette images to show the configuration of one or more of the devices held in the packaging, and directional arrows to indicate the direction the needles are to be introduced between a suprapubic and retropubic procedure (FIG. 12A).

Numerous configurations are possible for packaging of introducer systems, kits or devices. For instance, one configuration shown in FIG. 12A is a retropubic kit including, for example, two retropubic handles (e.g., handles 712) with two needles (e.g., needles 514) and a sheath assembly (e.g., sheath assembly 800). The needles may be pre-inserted into the handles. Other examples include a suprapubic kit (e.g., with two suprapubic needles 410 with handles 712 and sheath assembly 800), a retropubic/suprapubic kit (e.g., two handles 712, two retropubic needles 514, two suprapubic needles 410, and a sheath assembly 800), a TO hook kit (e.g., two hook needles 310 with handles 112 permanently molded thereon and a sheath assembly 800), a TO halo kit (e.g., two introducer devices 110, 210 and a sheath assembly 800), and a TO combination kit (e.g., two hook needles 310 with handles 112 permanently molded thereon, two introducer devices 110, 210, and a sheath assembly 800). Of course, other packaging configurations including devices and components described herein are also within the scope of the invention.

EXAMPLES OF SURGICAL PROCEDURES

Several methods are contemplated herein. Although the methods of use as disclosed herein generally relate to female incontinence conditions and treatments/procedures, male incontinence conditions and treatments/procedures are also included within the scope of the present invention. Further, the term "urethra," with respect to sling positioning, is used for brevity and reader convenience. It should be noted that the embodiments described herein are particularly suitable for placing a sling in a therapeutically effective position. The method may be utilized to support a variety of structures at different anatomical locations. Variations of these methods may occur due to individual surgeon's techniques or a patient's particular anatomy.

In accordance with one embodiment, a trans-obturator implant procedure is described. First, patient is positioned in a dorsal lithotomy position and prepared for surgery using standard operating procedures. Next, a surgeon makes a small vertical incision in the anterior vaginal wall beginning approximately 1 centimeter under the urethral meatus. The urethra is gently freed from the anterior vaginal wall. A scissor can then be used to dissect laterally in a 45 degree angle toward the ischiopubic ramus bone. The depth can then be checked digitally. These steps are repeated on the contralateral side.

The obturator fossa is then identified. This can be done by grasping the insertion of the adductor longus at its insertion to the pubic tubercle. By rocking a thumb under the adductor longus insertion, the superior portion of the obturator fossa can be identified. Next, two small skin incisions are made at the level of the clitoris in the fold of the thigh, facing the medial part of the obturator foramen.

The halo needle 114 is then inserted into of the skin incisions until the obturator membrane is perforated. The handle is orientated at approximately a 45 degree angle relative to the patients sagittal plane. Next, an index finger of the hand not holding the halo needle 114 can be placed in the ipsilateral dissection pouch. The halo needle 114 is guided behind the ischiopubic branch to meet the tip of the surgeon's index finger and guide the introducer tip 124 out of the vaginal incision. The surgeon's index finger can remain in contact with the tip 124 until the tip 124 is exteriorized. The connector 1000, which is already attached to a sheath assembly 800, can then be attached to the tip 124 of the halo needle 114. Detectable feedback of the connection can alert the surgeon the connector has been properly engaged. Traction can then be applied to the needle 114 or handle 612 to draw the sling tube 900 back through the skin incision. The above steps can then be repeated for the other side of the patient using the halo needle 214.

Next, a mesh sling is drawn into position within the sheath assembly, placing the tab 806, which is the mid-point of the mesh sling, under the mid-urethra. The two sides of the tab 806 are grasped and peeled away from the center of the sheath as indicated by the arrows on the tab 806. The tab 806 will then slide off of the two proximal ends of the sheath.

A blunt instrument is then placed between the urethra and the mesh while adjusting and positioning the sling. When the appropriate tension is attained, the sheath is removed to fully expose the mesh by pulling gently on both lateral ends of the sheath. The blunt instrument is kept in place under the urethra when removing the two ends of the sheath to ensure that over-tightening of the mesh does not occur. To complete the procedure, the exposed mesh strips are then cut at the level of the subcutaneous tissue and the skin incisions and vaginal incision are closed.

In accordance with one embodiment, a further trans-obturator implant procedure is described. First, patient is positioned in a dorsal lithotomy position and prepared for surgery using standard operating procedures. Next, a surgeon makes a small vertical incision in the anterior vaginal wall beginning approximately 1 centimeter under the urethral meatus. The urethra is gently freed from the anterior vaginal wall. A scissor can then be used to dissect laterally in a 45 degree angle toward the ischiopubic ramus bone. The depth can then be checked digitally. These steps are repeated on the contralateral side. The obturator fossa is then identified. This can be done by grasping the insertion of the adductor longus at its insertion to the pubic tubercle. By rocking a thumb under the adductor longus insertion, the superior portion of the obturator fossa can be identified. Next, two small skin incisions are made at the level of the clitoris in the fold of the thigh, facing the medial part of the obturator foramen.

The hook needle 310 is then inserted into of the skin incisions until the obturator membrane is perforated. The handle is then orientated at approximately a 45 degree angle relative to the patients sagittal plane. Next, an index finger of the hand not holding the hook needle 310 can be placed in the ipsilateral dissection pouch. The hook needle 310 is guided behind the ischiopubic branch to meet the tip of the surgeon's index finger and guide the introducer tip 324 out of the vaginal incision. The surgeon's index finger can remain in contact with the tip 324 until the tip 324 is exteriorized. The connector 1000, which is already attached to a sheath assembly 800, can then be attached to the tip 324 of the hook needle 310. Detectable feedback of the connection can alert the surgeon the connector has been properly engaged. Traction can then be applied to the hook needle 310 or handle 612 to draw the sling tube 900 back through the skin incision. The foregoing steps can then be repeated for the other side of the patient using a second hook needle similar to, or the same as, hook needle 310.

Next, a mesh sling is drawn into position within the sheath assembly, placing the tab 806, which is the mid-point of the mesh sling, under the mid-urethra. The two sides of the tab 806 are grasped and peeled away from the center of the sheath as indicated by the arrows on the tab 806. The tab 806 will then slide off of the two proximal ends of the sheath. A blunt instrument is then placed between the urethra and the mesh while adjusting and positioning the sling. When the appropriate tension is attained, the sheath is removed to fully expose the mesh by pulling gently on both lateral ends of the sheath. The blunt instrument is kept in place under the urethra when removing the two ends of the sheath to ensure that over-tightening of the mesh does not occur. To complete the procedure, the exposed mesh strips are then cut at the level of the subcutaneous tissue and the skin incisions and vaginal incision are closed.

In accordance with another embodiment, a suprapubic implant procedure is described. First, the lower abdominal and vaginal operative sites are prepared using normal surgical procedures. Next, two small abdominal incisions, approximately 1.5-2.0 cm in size, are made on each side of the midline just above the symphysis. Also, a small vertical incision is made in the anterior vaginal wall beginning approximately 1 cm under the urethral meatus. The urethra is gently freed from the anterior vaginal wall. Next, two small paraurethral dissections are made bilaterally to prepare for introducer insertion.

The needle 410 is inserted into one of the abdominal incisions. Using the posterior surface of the pubic bone, the needle 410 is then walked down toward the vaginal incision. Using the index finger of the other hand to meet the tip 424, the needle 410 is guided through the endopelvic fascia and into the vaginal incision. The connector 1000, which is already attached to a sheath assembly 800, is then attached to the tip 424 of the needle 410. Detectable feedback of the connection can alert the surgeon that the connector has been properly engaged. The needle 410 is then grasped and the sheath assembly is drawn up through the abdominal incision until the beginning of the tube 900 is visualized through the abdominal incision. The foregoing steps are repeated on the patient's contralateral side using a second needle introducer similar to, or the same as, needle 410. Once this is done, the tubes 900 should be in place and cystoscopy can be performed to confirm bladder integrity.

Next, a mesh sling is drawn into position within the sheath assembly, placing the tab 806, which is the mid-point of the mesh sling, under the mid-urethra. The two sides of the tab 806 are grasped and peeled away from the center of the sheath as indicated by the arrows on the tab 806. The tab 806 will then slide off of the two proximal ends of the sheath. A blunt instrument is then placed between the urethra and the mesh while adjusting and positioning the sling. When the appropriate tension is attained, the sheath is removed to fully expose the mesh by pulling gently on both lateral ends of the sheath. The blunt instrument is kept in place under the urethra when removing the two ends of the sheath to ensure that over-tightening of the mesh does not occur. To complete the procedure, the exposed mesh strips are then cut at the level of the subcutaneous tissue and the skin incisions and vaginal incision are closed.

In accordance with another embodiment, a retropubic implant procedure is described. First the lower abdominal and vaginal operative sites are prepared using normal surgical procedures. Next, two small abdominal incisions, approximately 1.5-2.0 cm in size, are made on each side of the midline just above the symphysis. Also, a small vertical incision is made in the anterior vaginal wall beginning approximately 1 cm under the urethral meatus. The urethra is gently freed from the anterior vaginal wall. Next, two small paraurethral dissections are made bilaterally to prepare for introducer insertion.

By first resting the tip 524 on the palmar surface of the non-dominant index finger, the needle 514 is inserted into one of the paraurethral spaces and the endopelvic fascia is perforated. The needle 514 is then guided through the space of Retzius and the rectus sheath and muscle are perforated. Next, the needle 514 is guided to the abdominal incision until the needle 514 is exposed through the incision. In a next step, the button 762 of the handle 712 is depressed and the needle 514 is disconnected from the handle 712 by sliding the handle 712 away from the patient. The connector 1000, which is already attached to a sheath assembly 800, is then attached to a distal end of the needle 515. Detectable feedback of the connection can alert the surgeon that the connector 100 has been properly engaged. The needle 514 is then grasped and the sheath assembly is drawn up through the abdominal incision until the beginning of the tube 900 is visualized through the abdominal incision. The foregoing steps are repeated on the patient's contralateral side using a second needle introducer similar to, or the same as, needle 514. Once this is done, the tubes 900 should be in place and cystoscopy can be performed to confirm bladder integrity.

Next, a mesh sling is drawn into position within the sheath assembly, placing the tab 806, which is the mid-point of the mesh sling, under the mid-urethra. The two sides of the tab 806 are grasped and peeled away from the center of the sheath as indicated by the arrows on the tab 806. The tab 806 will then slide off of the two proximal ends of the sheath. A blunt instrument is then placed between the urethra and the mesh while adjusting and positioning the sling. When the appropriate tension is attained, the sheath is removed to fully expose the mesh by pulling gently on both lateral ends of the sheath. The blunt instrument is kept in place under the urethra when removing the two ends of the sheath to ensure that over-tightening of the mesh does not occur. To complete the procedure, the exposed mesh strips are then cut at the level of the subcutaneous tissue and the skin incisions and vaginal incision are closed.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An introduction device for an implant, comprising:
 a handle, a first plane bisecting the handle between a top and a bottom thereof along a longitudinal axis; and
 an elongate member having a proximal end including a straight segment coupled to the handle and a distal end terminating in a tip, the elongate member including a first curved portion and a second curved portion, the entire second curved portion lying along a second plane perpendicular to the first plane, and the second curved portion touching the first plane at a first location along a path of the second curved portion from a proximal end of the second curved portion to a distal end of the second curved portion thereof and at a second location distal of the first location along the path.

2. The introduction device according to claim 1, a space above the first plane including the top of the handle and a space below the first plane including the bottom of the handle, wherein the first curved portion lies substantially below the first plane.

3. The introduction device according to claim 2, wherein a distal end of the first curved portion is connected to a proximal end of the second curved portion.

4. The introduction device according to claim 1, wherein the first location is adjacent a proximal end of the second curved portion and the second location is adjacent a distal end of the second curved portion.

5. The introduction device according to claim 1, a third plane bisecting the handle between opposing sides thereof, the third plane perpendicular to the first plane and the second plane, wherein the second curved portion passes through the third plane.

6. The introduction device according to claim 5, wherein the second curved portion is asymmetrical with respect to the third plane.

7. The introduction device according to claim 6, wherein the second curved portion includes a first arc from the proximal end of the second curved portion to the third plane and a second arc from the third plane to the distal end of the second curved portion.

8. The introduction device according to claim 7, wherein the first arc has a radius of curvature greater than a radius of curvature of the second arc.

9. The introduction device according to claim 5, wherein a first length measured along a straight line in the second plane from the proximal end of the second curved portion to the third plane is greater than a second length measured along a straight line in the second plane from the third plane to the distal end of the second curved portion.

10. The introduction device according to claim 1, wherein a distal end of the first curved portion is connected to the proximal end of the second curved portion at a transition region.

11. The introduction device according to claim 1, wherein the distal end of the second curved portion is substantially parallel to a third plane.

12. The introduction device according to claim 11, wherein a proximal end of the first curved portion is connected to a distal end of the straight segment at a transition region.

13. The introduction device according to claim 1, wherein the tip includes a first tip portion, a second tip portion connected to the first tip portion, and a third tip portion connected to the second tip portion, the first tip portion, the second tip portion and the third tip portion having different shapes.

14. A kit for introducing an implant, comprising:
a first introduction device, comprising a first handle having a length extending along a first longitudinal axis and being bisected by a first longitudinal plane extending along the first longitudinal axis, and a first elongate member having a proximal end coupled to a distal end of the first handle, the first elongate member including a first curved portion, the first curved portion lying entirely along a first perpendicular plane that is perpendicular to the first longitudinal axis, a first path along the first curved portion from a proximal end to a distal end thereof traveling in a first direction, the first curved portion touching the first longitudinal plane at a first location along the first path and at a second location distal of the first location along the first path; and a second introduction device, comprising a second handle having a length extending along a second longitudinal axis and being bisected by a second longitudinal plane extending along the second longitudinal axis, and a second elongate member having a proximal end coupled to a distal end of the second handle, the second elongate member including a second curved portion, the second curved portion lying entirely along a second perpendicular plane that is perpendicular to the second longitudinal axis, a second path along the second curved portion from a proximal end to a distal end traveling in a second direction opposite the first direction, the second curved portion touching the second longitudinal plane at a first location along the second path and at a second location distal of the first location along the second path.

15. The kit according to claim 14, further comprising an implant including a sheath assembly and a mesh implant at least partially covered by the sheath assembly.

16. An introducer needle comprising:
a proximal section including a feature that enables engagement with a handle;
a distal section; and
an intermediate section disposed between the proximal section and the distal section, the introducer needle including, from a proximal end to a distal end thereof, a straight section along a longitudinal axis, a first curved section, and a second curved section lying entirely along a plane perpendicular to the longitudinal axis, the first curved section lying along a separate plane and having a radius of curvature along the separate plane greater than a radius of curvature of the second curved section along the plane perpendicular to the longitudinal axis.

17. The introducer needle according to claim 16, wherein the distal section is substantially in a plane perpendicular to at least a portion of the proximal section.

18. The introducer needle according to claim 16, wherein the proximal section is straight and is attached to the handle.

19. The introducer needle according to claim 16, wherein the intermediate section is disposed at an angle relative to the proximal and distal sections.

* * * * *